United States Patent [19]
Stern et al.

[11] Patent Number: 5,562,720
[45] Date of Patent: Oct. 8, 1996

[54] BIPOLAR/MONOPOLAR ENDOMETRIAL ABLATION DEVICE AND METHOD

[75] Inventors: Roger A. Stern, Cupertino; Vincent N. Sullivan, San Jose; Roxanne L. Richman, Santa Cruz; Loren L. Roy, Northridge; Robert L. Marion; Thomas D. Striegler, both of San Jose, all of Calif.

[73] Assignee: Vesta Medical, Inc., Palo Alto

[21] Appl. No.: 319,216

[22] Filed: Oct. 6, 1994

Related U.S. Application Data

[63] Continuation-in-part of Ser. No. 877,567, May 1, 1992, Pat. No. 5,277,201, and a continuation-in-part of Ser. No. 46,683, Apr. 14, 1993, Pat. No. 5,443,470, and a continuation-in-part of Ser. No. 106,601, Aug. 16, 1993, Pat. No. 5,443,463, and a continuation-in-part of Ser. No. 136,098, Oct. 14, 1993, abandoned.

[51] Int. Cl.⁶ ........................................................ A61N 5/00
[52] U.S. Cl. .................................. 607/98; 607/99; 606/32; 606/41
[58] Field of Search .......................... 607/98, 99; 606/32, 606/33, 34, 37–40, 41, 48–50

[56] References Cited

U.S. PATENT DOCUMENTS

| | | |
|---|---|---|
| 1,827,306 | 10/1931 | Chapman et al. . |
| 3,324,847 | 6/1967 | Zoumboulis . |
| 3,369,549 | 2/1968 | Armao . |
| 3,750,653 | 8/1973 | Simon . |
| 3,789,829 | 2/1974 | Hassen . |

(List continued on next page.)

FOREIGN PATENT DOCUMENTS

| | | |
|---|---|---|
| 0115420 | 8/1984 | European Pat. Off. . |
| 0407057 | 1/1991 | European Pat. Off. . |
| 2573301 | 11/1984 | France . |
| 2679456 | 1/1993 | France . |
| 8527331.7 | 9/1985 | Germany . |
| 3516830 | 11/1986 | Germany . |
| WO87/01276 | 3/1987 | WIPO . |
| WO90/07303 | 12/1990 | WIPO . |

OTHER PUBLICATIONS

"Hyperthermia Overview Using Microwave Antennas", Invited Lectures, Thomas P. Ryan, M.D. Thermoradiotherapy, C. T. Coughlin, M.D.
"Devices: Replaceing The Roto–Rooter", Trends, Michael Dolan.
"Endometrial Ablation", Therapeutic Hysteroscopy: Indications and Techniques, pp. 148–163, W. W. Babcock et al.
"Uterine Resectoscopes for Endometrial Ablation and Resection", Karl Storz.

(List continued on next page.)

*Primary Examiner*—Lee S. Cohen
*Attorney, Agent, or Firm*—William B. Walker

[57] ABSTRACT

An endometrial ablation device and a method of manufacturing and using the device. An RF current is passed through an endometrium to heat it. An electroconductive expandable member such as a balloon is used as the medium for passing the current and causing the heating of the endometrium. The power delivered from a power source to the balloon is selectively provided to a plurality of electrode area segments on the balloon with each of the segments have a thermistor associated with it whereby temperature is monitored and controlled by a feedback arrangement from the thermistors. The selective application of power is provided on the basis of a switching arrangement which provides either monopolar or bipolar energy to the electrodes. The method of manufacturing the ablation device includes using commercially available stretchable sheet material or providing a mandrel or support base and coating the mandrel or base with an uncured emulsion. The emulsion is then cured to form a bladder-like coating. The coating is thereafter removed from the mandrel or base to form a bladder. Electrons and temperature sensors are formed on or secured to the bladder during or after the curing process and a fluid delivery tube is secured to the bladder for inflating the bladder.

4 Claims, 19 Drawing Sheets

U.S. PATENT DOCUMENTS

| | | |
|---|---|---|
| 3,840,016 | 10/1974 | Lindemann . |
| 3,901,224 | 8/1975 | Bucalo . |
| 3,924,628 | 12/1975 | Droegemueller et al. . |
| 3,934,580 | 1/1976 | Cournut . |
| 4,014,988 | 3/1977 | Pharriss et al. . |
| 4,016,270 | 4/1977 | Pharriss et al. . |
| 4,051,855 | 10/1977 | Schneiderman . |
| 4,072,147 | 2/1978 | Hett . |
| 4,102,342 | 7/1978 | Akiyama et al. . |
| 4,160,455 | 7/1979 | Law . |
| 4,198,981 | 4/1980 | Sinnreich . |
| 4,244,371 | 1/1981 | Farin . |
| 4,292,960 | 10/1981 | Paglione . |
| 4,296,760 | 10/1981 | Carlsson et al. . |
| 4,311,154 | 1/1982 | Sterzer et al. . |
| 4,349,033 | 9/1982 | Eden . |
| 4,375,220 | 3/1983 | Matvias . |
| 4,377,168 | 3/1983 | Rzasa et al. . |
| 4,409,993 | 10/1983 | Furihata . |
| 4,469,103 | 9/1984 | Barrett . |
| 4,491,131 | 1/1985 | Vassiliadis . |
| 4,494,539 | 1/1985 | Zenitani et al. . |
| 4,549,533 | 10/1985 | Cain et al. . |
| 4,552,127 | 11/1985 | Schiff . |
| 4,572,190 | 2/1986 | Azam et al. . |
| 4,622,972 | 11/1986 | Giebeler, Jr. . |
| 4,638,436 | 1/1987 | Badger et al. . |
| 4,655,216 | 4/1987 | Tischer . |
| 4,658,836 | 4/1987 | Turner . |
| 4,662,383 | 5/1987 | Sogawa et al. . |
| 4,674,481 | 6/1987 | Boddie, Jr. et al. . |
| 4,676,258 | 6/1987 | Inokuchi et al. . |
| 4,692,452 | 9/1987 | Cerny et al. . |
| 4,700,701 | 10/1987 | Montaldi . |
| 4,709,698 | 12/1987 | Johnston et al. . |
| 4,754,752 | 7/1988 | Ginsburg et al. . |
| 4,754,757 | 7/1988 | Feucht . |
| 4,758,592 | 7/1988 | Horrobin et al. . |
| 4,771,778 | 9/1988 | Mar . |
| 4,773,899 | 9/1988 | Spears . |
| 4,776,349 | 11/1988 | Nashef et al. . |
| 4,818,954 | 4/1989 | Flachenecker et al. . |
| 4,823,812 | 4/1989 | Eshel et al. . |
| 4,836,189 | 6/1989 | Allred, III et al. . |
| 4,852,579 | 8/1989 | Gilstad et al. . |
| 4,860,752 | 8/1989 | Turner . |
| 4,865,047 | 9/1989 | Chou et al. . |
| 4,927,413 | 5/1990 | Hess . |
| 4,935,003 | 6/1990 | Gainutdinova et al. . |
| 4,938,217 | 7/1990 | Lele . |
| 4,946,440 | 8/1990 | Hall . |
| 4,949,718 | 8/1990 | Newwirth et al. . |
| 4,955,377 | 9/1990 | Lennox et al. . |
| 4,960,109 | 10/1990 | Lele . |
| 4,961,435 | 10/1990 | Kitagawa et al. . |
| 4,967,765 | 11/1990 | Turner et al. . |
| 4,974,587 | 12/1990 | Turner et al. . |
| 4,979,948 | 12/1990 | Geddes et al. . |
| 4,985,027 | 1/1991 | Dressel . |
| 4,993,430 | 2/1991 | Shimoyama et al. . |
| 4,997,653 | 3/1991 | Igarashi . |
| 4,998,930 | 3/1991 | Lundahl . |
| 5,003,991 | 4/1991 | Takayama et al. . |
| 5,006,119 | 4/1991 | Acker et al. . |
| 5,026,959 | 6/1991 | Ito et al. . |
| 5,032,124 | 7/1991 | Menton . |
| 5,035,694 | 7/1991 | Kasprzyk et al. . |
| 5,041,089 | 8/1991 | Mueller et al. . |
| 5,045,056 | 9/1991 | Behl . |
| 5,050,597 | 9/1991 | Daikuzono . |
| 5,057,106 | 10/1991 | Kasevich et al. . |
| 5,059,191 | 10/1991 | Beyer et al. . |
| 5,084,044 | 1/1992 | Qunit . |
| 5,092,841 | 3/1992 | Spears . |
| 5,098,429 | 3/1992 | Sterzer . |
| 5,100,388 | 3/1992 | Behl et al. . |
| 5,122,137 | 6/1992 | Lennox . |
| 5,188,122 | 1/1993 | Phipps et al. . |
| 5,190,541 | 3/1993 | Abele et al. . |
| 5,248,312 | 9/1993 | Langberg . |
| 5,257,635 | 11/1993 | Langberg ................................. 606/41 |
| 5,693,563 | 9/1987 | Cerny et al. . |

OTHER PUBLICATIONS

"Treatment of Menorrhagia by Radiofrequency Heating", Int. J. Hyperthermai, 1991, vol. 7, No. 2, 213–220, M. V. Prior et al.

"Treatment of Functional Menorrhagia by Radiofrequency–Induced Thermal Endometrial Ablation", The Lancet, Feb. 17, 1990, pp. 374–376, J. H. Phipps et al.

"Resectoscopes for the Gynecologist", Contemporary OB/GYN, Philip G. Brooks, M.D., pp. 51–57.

"New Techniques in Operative Hysteroscopy", Audio–Digest Obstetrict/Gynecology, vol. 37, No. 10, May 15, 1990, Bruce McLucas et al.

"New Concepts in Hysteroscopy", Symposium, Contemporary OB/GYN, pp. 84–103, Michael S. Baggish, M.D. et al.

"Microwave Applicator for Transurethral Hyperthermia of Benign Prostatic Hyperplasia", Int. J. Hyperthermia, 1989, vol. 5, No. 3, 283–296, H. A. Astrahan et al.

"Endometria Ablatin: An Alternative to Hysterectomy", The American Journal of Gynecologic Healt h, vol. V, No. 3, Thierry G. Vancaillie, M.D.

"A Technique for Combining Microwave Hyperthermia with Intraluminal Brachytherapy of the Oesophagus", Int. J. Hyperthermia, 1989, vol. 5, No. 1, 37–51, M. A. Astrahan et al.

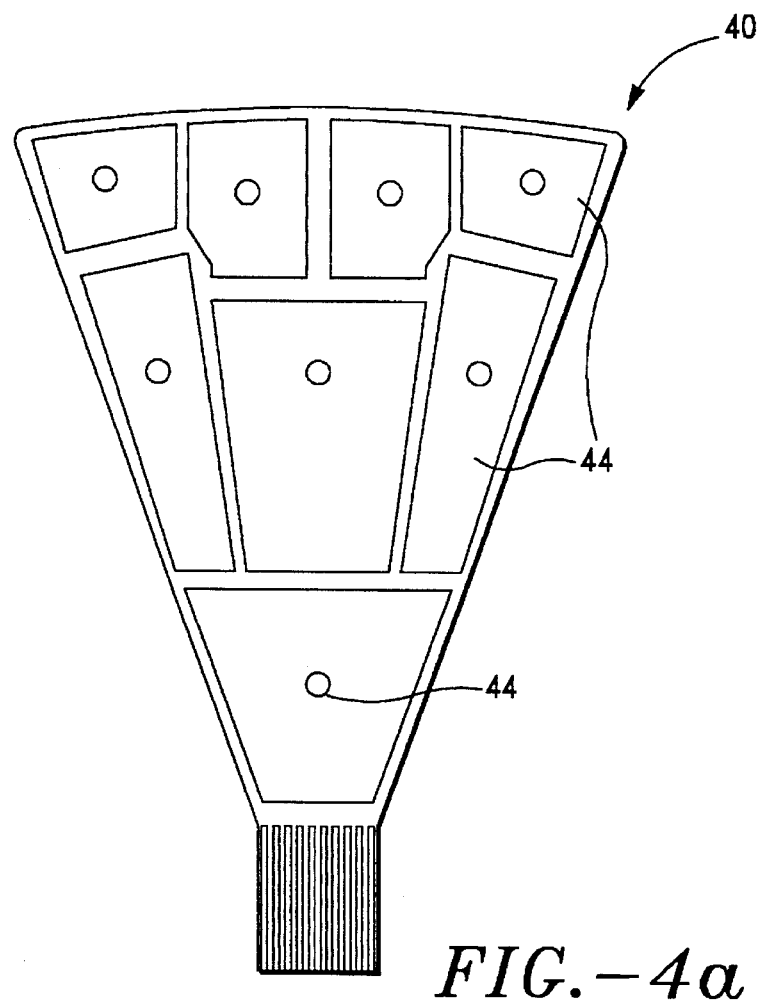
FIG.—4a
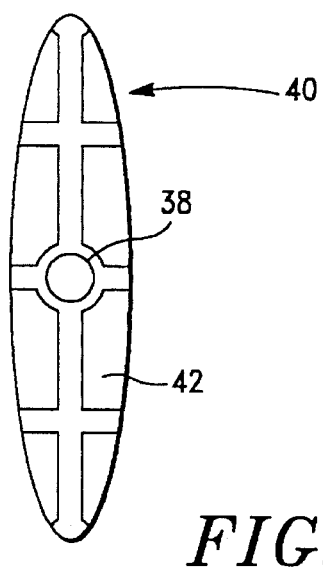
FIG.—4b

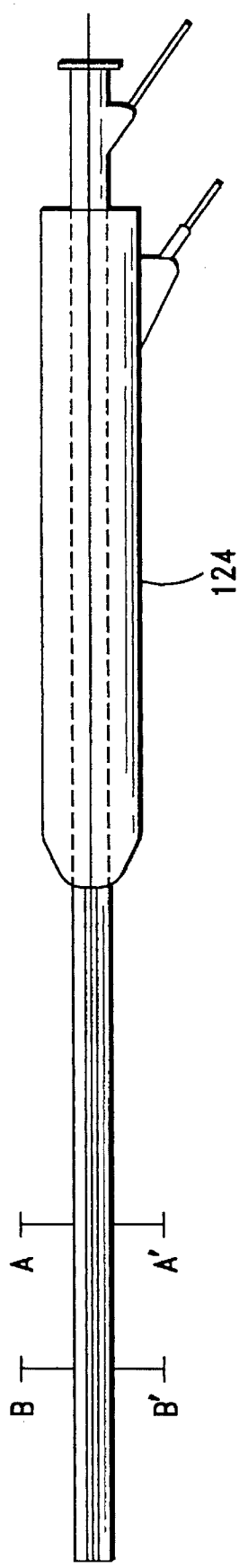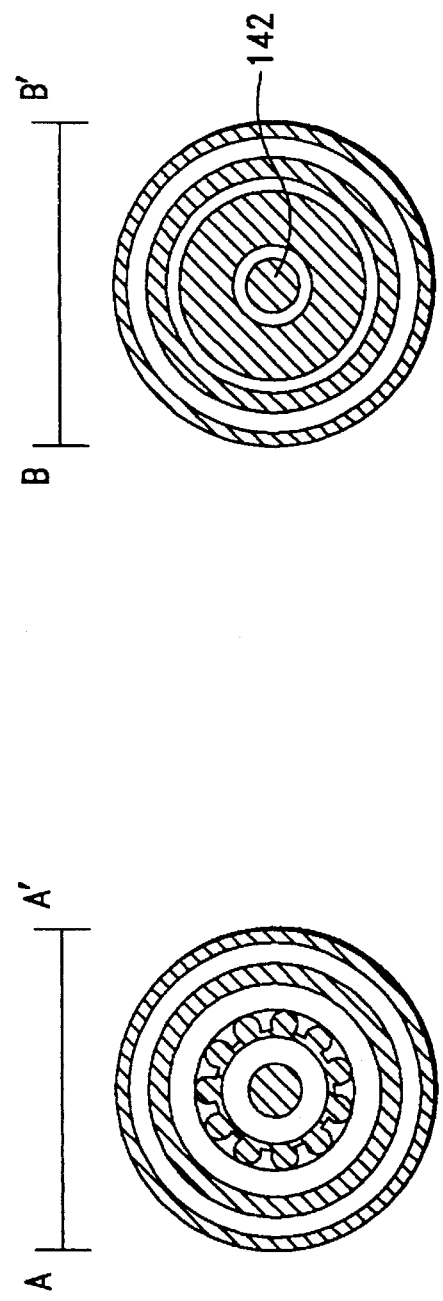
FIG. 11a
FIG. 11b
FIG. 11c

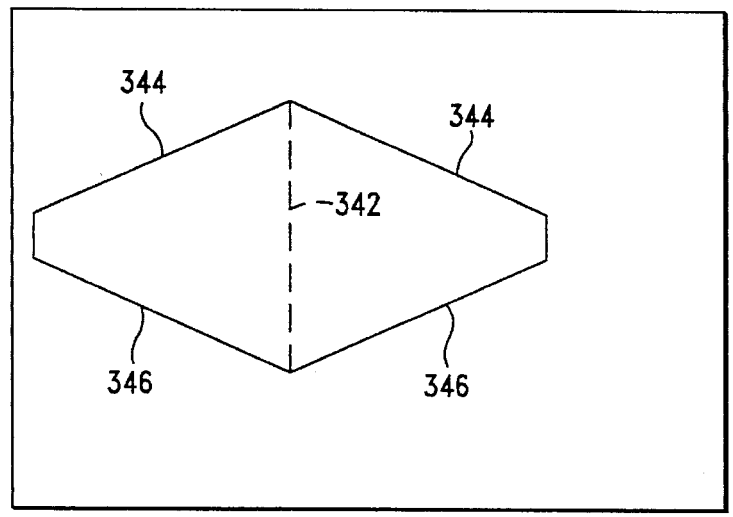
*FIG.−21*
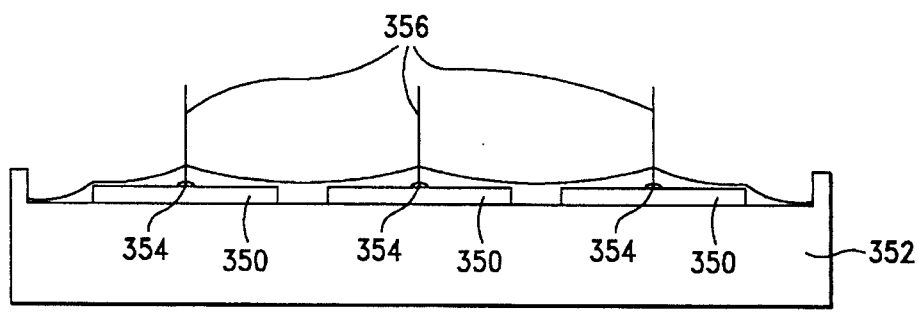
*FIG.−22*
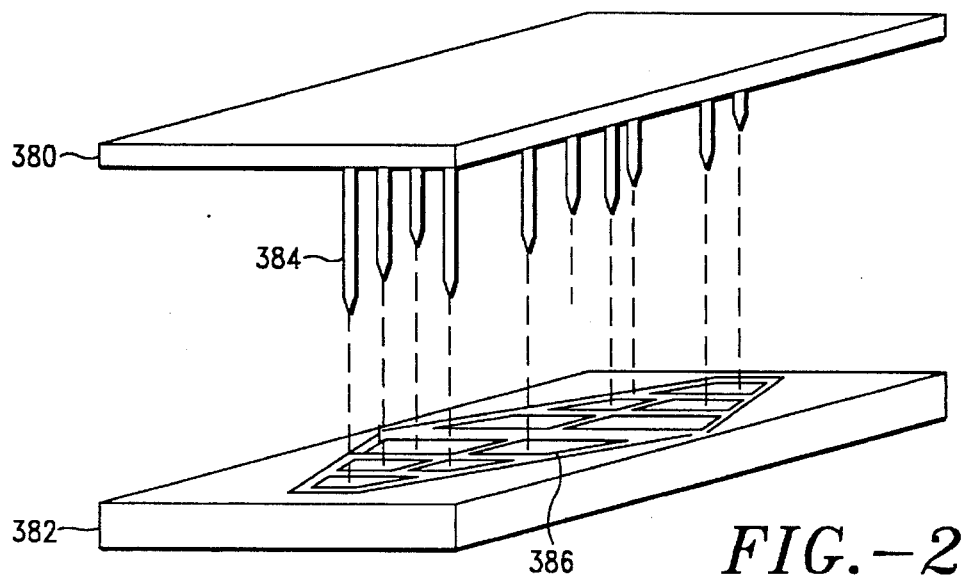
*FIG.−25*

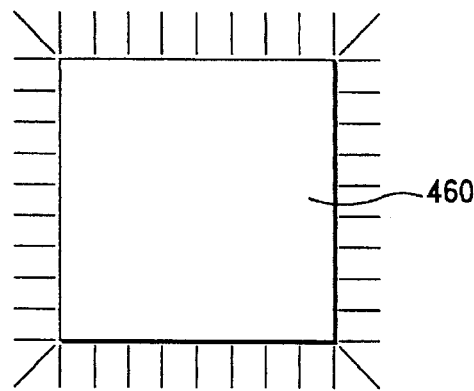
FIG.—34
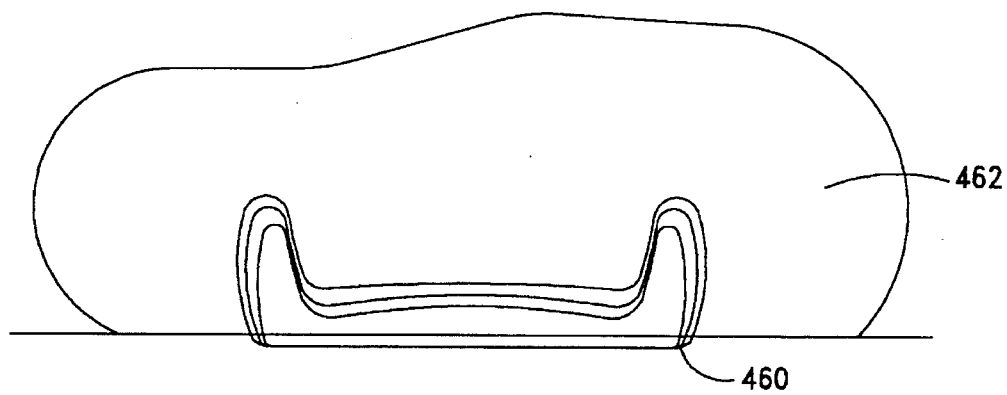
FIG.—35
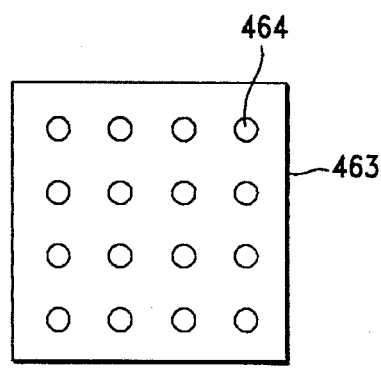
FIG.—36

BIPOLAR/MONOPOLAR ENDOMETRIAL ABLATION DEVICE AND METHOD

CROSS-REFERENCE TO RELATED APPLICATION

This is a continuation-in-part of application Ser. No. 07/877,567 filed May 1, 1992, now U.S. Pat. No. 5,277,201, and application Ser. No. 08/046,683, filed Apr. 14, 1993, now U.S. Pat. No. 5,443,470, and application Ser. No. 08/106,601 filed Aug. 16, 1993, now U.S. Pat. No. 5,443,463, and application Ser. No. 08/136,098 filed Oct. 14, 1993 now abandoned.

BACKGROUND OF THE INVENTION

1. Field of the Invention

The present invention relates to a method and an apparatus for in situ destruction of the inner lining of body organs, and more particularly the providing of a selective destruction of the endometrium with selective use of a bipolar/monopolar application of RF energy as an alternative to hysterectomy for treatment of uterine bleeding. It also relates to a method of manufacturing such an apparatus.

2. Discussion of Background

Prior techniques for removing or destroying the inner lining of body organs have been explored in order to provide for an alternative to surgical removal of the body organs for treatment of diseases and other abnormal conditions. Prior techniques involved the destructive treatment of the inner linings with chemicals and with various forms of thermal energy such as radio frequency, microwave heating, cryotherapy, laser surgery and electrosurgery. Radio frequency and microwave energies have also been applied directly to the linings to generate heat in situ.

One type of thermal destruction is described in U.S. Pat. No. 4,979,949 wherein thermal ablation of the mucosal layer of a gall bladder is accomplished by resistive heating with an RF balloon electrode. Electric current is delivered from an electrode in the center of the balloon by a conductive expansion liquid filling the balloon. This device has power loss which occurs in the conductive fluid, and it cannot be adapted for anything but a single electrode arrangement.

In another example of prior art treatment, balloon catheters have been supplied with a heated fluid for thermal ablation of hollow body organs as described in U.S. Pat. No. 5,045,056. Furthermore, application of microwave and high frequency RF energy to body areas to destroy body tissue, using single electrodes enclosed in expanded balloons have been described in U.S. Pat. No. 4,662,383 and U.S. Pat. No. 4,676,258.

The disadvantage of the procedures occurring in the prior art such as described above include a lack of uniform large area treatment because these procedures involve a lack of uniform control or temperature sensing ability to ensure complete ablation.

Other procedures developed to date involve manual applications of small treatment tools to successive areas of the lining which is an expensive operating room procedure and which, similar to the other previous heat balloon treatments, involve limited assurance of uniform results.

OBJECTS AND SUMMARY OF THE INVENTION

Accordingly, one object of the present invention is to provide a novel method and apparatus for performing safe and rapid endometrial ablation without the need for visual contact during the ablation of the lining.

It is a further object to provide an apparatus and a method for endometrial ablation which can be carried out on an out-patient basis without requiring the use of an operating room.

The objects of the invention are carried out by a method which utilizes an expandable member conforming to the inner surface of the endometrium. The outer surface of the expandable member contains one or more electrodes, and the member is filled with an electrically non-conductive medium. RF current is passed through substantially the entire surface of the endometrium by activating the electrodes. The current is sufficient to resistively heat the endometrium in a single operation to a temperature within a range of between 45° C. to 90° C. for a time sufficient to destroy the cells of the lining while maintaining the average temperature of the myometrium at a temperature of substantially 42° C. or less. The RF current has a frequency of at least 250 kHz and less than 100 MHz.

The method according to the present invention involves the insertion of a conductive, expandable member in its unexpanded state into the uterine cavity through the cervical opening and subsequently expanding the member to establish surface contact with the endometrial surface and applying the RF current to the member in its expanded condition.

It is a further object of the present invention to provide that the electroconductive expandable member includes a thin bladder having an array of separate electrodes on one surface and further having a temperature sensor such as a thermistor associated with each separate electrode in order to provide a feedback temperature for each electrode. The plurality of separate electrodes are independently and sequentially energized and controlled with thermistor temperature feedback control to bring the endometrial temperature to a desired level.

It is a further object of the present invention to provide a system of selective delivery of either monopolar RF energy to a single electrode or bipolar RF energy to chosen pairs of an array of separate electrodes which are used to bring the endometrial temperature to a desired level.

It is further an object of the present invention to provide electrodes having a specific configuration so that the heating is not concentrated at the edges of the electrode and so that uniform heating is achieved over the entire electrode surface by providing a plurality of throughholes throughout the electrode or by forming the electrode in a pattern of lines, thereby creating a uniform density of edges and equalizing the current density across the surface area of the electrode.

It is a further object of the present invention to provide an electronic control means capable of controlling the output of a conventional electrosurgical power source and delivering power from the power source sequentially, and in a controlled manner, to the electrodes of the balloon.

It is a further object of the present invention to provide a disposable handheld applicator and electrode assembly combination to deliver the ablation device to the uterus and to retract the device upon completion of the ablation.

It is a further object of the present invention to provide an array of separate electrodes and associated separate thermistors on an expandable member with a series of power leads with each power lead delivering power to a single electrode and serving as one conductor to its associated thermistor to provide a temperature feedback for temperature regulation of the endometrial ablation.

It is a further object of the present invention to provide an inner lumen having the ability to contain a fiber optic image conduit which serves as a visual aid when placing the device.

It is a further object of the present invention to provide control means to operate the electrode balloon in a monopolar, bipolar, or both monopolar and bipolar modes.

In particular it is an object of the invention to provide a bladder which is made of a stretchable material in order to accommodate various sizes and shapes of uteri.

It is yet a further object of the invention to provide a variety of methods for manufacturing an ablation device of the invention.

According to the invention there is provided an apparatus for selectively applying RF energy to a body organ. The apparatus comprises an electrode means for effecting electrical contact with tissue of said body organ; a radio frequency power means for selectively providing current to said electrode means at a frequency greater than 250 kHz to heat said tissue at a uniform temperature between 45° C. and 90° C.; and switching means for receiving an output from said radio frequency power means and for providing controllable delivery of power to said electrodes wherein said switching means includes a first means for providing bipolar energy to said electrode means, a second means for providing monopolar energy to said electrode means, and a third means for selecting one of said first and second means. The first means can include a means for delivering said RF energy in a bipolar mode between selected ones of a plurality of electrodes.

Further according to the invention there is provided a method of heating body organ tissue by the selective application of RF energy to said tissue, comprising the steps of providing a plurality of electrodes in electrical contact with said body organ providing a source of radio frequency energy to said plurality of electrodes and controlling said radio frequency energy to provide for one of bipolar and monopolar application of energy to said plurality of electrodes. The step of controlling said radio frequency energy can include selectively providing bipolar energy to selective pairs of said plurality of electrodes.

Still further according to the invention there is provided a method of manufacturing an ablation device which includes providing a mandrel; securing electrodes to the mandrel; coating the mandrel with an uncured emulsion; curing the emulsion to form a bladder-like coating over the mandrel; and removing the coating from the mandrel. The step of securing the electrodes to the mandrel can include securing the electrodes by means of an adhesive. The step of coating the mandrel can include dipping the mandrel into the uncured emulsion. The emulsion can comprise silicone rubber. The mandrel can be collapsible and the step of removing the coating from the mandrel can include collapsing the mandrel.

Still further according to the invention there is provided a method of manufacturing an ablation device which includes providing a planar stretchable sheet material having two major surfaces; securing at least one electrode to one of the surfaces; passing a conductor to each electrode through the layer; folding the layer in half along a fold line; and securing the two layer halves to each other along two seal lines to define a bladder with an opening.

Still further according to the invention there is provided a method of manufacturing an ablation device which includes providing a support base having a substantially planar surface; coating the surface of the support with an uncured emulsion; curing the emulsion to form a layer of stretchable material having two major surfaces; removing the layer from the support; securing at least one electrode to one of the surfaces; passing a conductor to each electrode through the layer; folding the layer in half along a fold line; and securing the two layer halves to each other along two seal lines to define a bladder with an opening.

Still further according to the invention there is provided a method of manufacturing an ablation device which includes providing a support base having a substantially planar surface; securing at least one electrode to the surface of the support, each electrode having a conductor extending from the electrode; depositing an uncured emulsion onto the surface of the support to embed the electrodes in the emulsion and to form a seal around the conductors extending from the electrodes; curing the emulsion to form a layer having two major surfaces; removing the layer; folding the layer in half along a fold line; and securing the two layer halves to each other along two seal lines to define a bladder having an opening. The step of securing at least one electrode to the surface of the support base can include securing the electrode by means of an adhesive. The support base can include an electrode support zone for each electrode and a channel extending to each support zone, and wherein the step of securing at least one electrode to the surface of the support base includes sucking air through the channels to secure each electrode by means of suction or vaccuum. The step of depositing an uncured emulsion can include depositing silicone rubber onto the surface and the at least one electrode. The emulsion can be a room temperature cured emulsion and the curing of the emulsion can include allowing the emulsion to cure slowly at substantially room temperature. The emulsion can be a heat cured emulsion and the step of curing the emulsion can include heating the emulsion. The step of securing the two layer halves to each other can include securing the two layer halves to each other by means of an adhesive. The support base can include depressions defining electrode supporting zones for supporting the electrodes. The step of securing at least one electrode to the surface can include depositing an adhesive layer into each supporting zone. Depositing the layer of adhesive into each supporting zone can include transferring the adhesive in the form of an adhesive island for each supporting zone from an adhesive island support sheet to each supporting zone by placing the sheet over the at least one supporting zone. The method can include the step of securing a temperature sensor to at least one of the electrodes. Each temperature sensor can be secured to its electrode by depositing the uncured emulsion over the temperature sensor so as to embed the temperature sensor in the bladder and against the electrode. The method can include securing a tube for delivering fluid and for optical viewing to the opening of the bladder. The method can include mounting a second tube on the surface of the support base prior to depositing the uncured emulsion onto the surface to provide the bladder with a central lumen. The method can include mounting a moveable sleeve over the fluid delivery tube.

Still further according to the invention there is provided an ablation device comprising an expandable bladder having an opening; at least one electrode defined on the bladder; and a fluid delivery tube secured to the bladder so as to be in communication with the opening. The ablation device can include a temperature sensor mounted on at least one of the electrodes. The ablation device can include a tube extending through the bladder and opening to an outer surface of the bladder at a distal end of the bladder. The ablation device can include a moveable sleeve movably mounted over the fluid delivery tube. The ablation device can include a catheter for receiving the fluid delivery tube and bladder.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4a–b is a representation of an embodiment of an expandable member which uses a plurality of surface segments with each surface segment having a separate conductive surface and a temperature sensor;

FIGS. 11a–c show the bladder device of FIG. 10 in a retracted position and illustration of the deflated expandable member;

FIG. 21 is a schematic plan view of a layer of stretchable material for use in manufacturing an ablation balloon in accordance with the invention;

FIG. 22 is a sectional side view of an ablation balloon in the process of being manufactured;

FIG. 25 is an isometric view of yet another support base arrangement;

FIG. 34 is a schematic plan view of an electrode showing the electric field distribution;

FIG. 35 is a side view of the electrode of FIG. 34, schematically showing the heat distribution generated by the electrodes;

FIG. 36 is a plan view of one embodiment of an electrode;

DETAILED DESCRIPTION OF THE PREFERRED EMBODIMENTS

Figure 1:
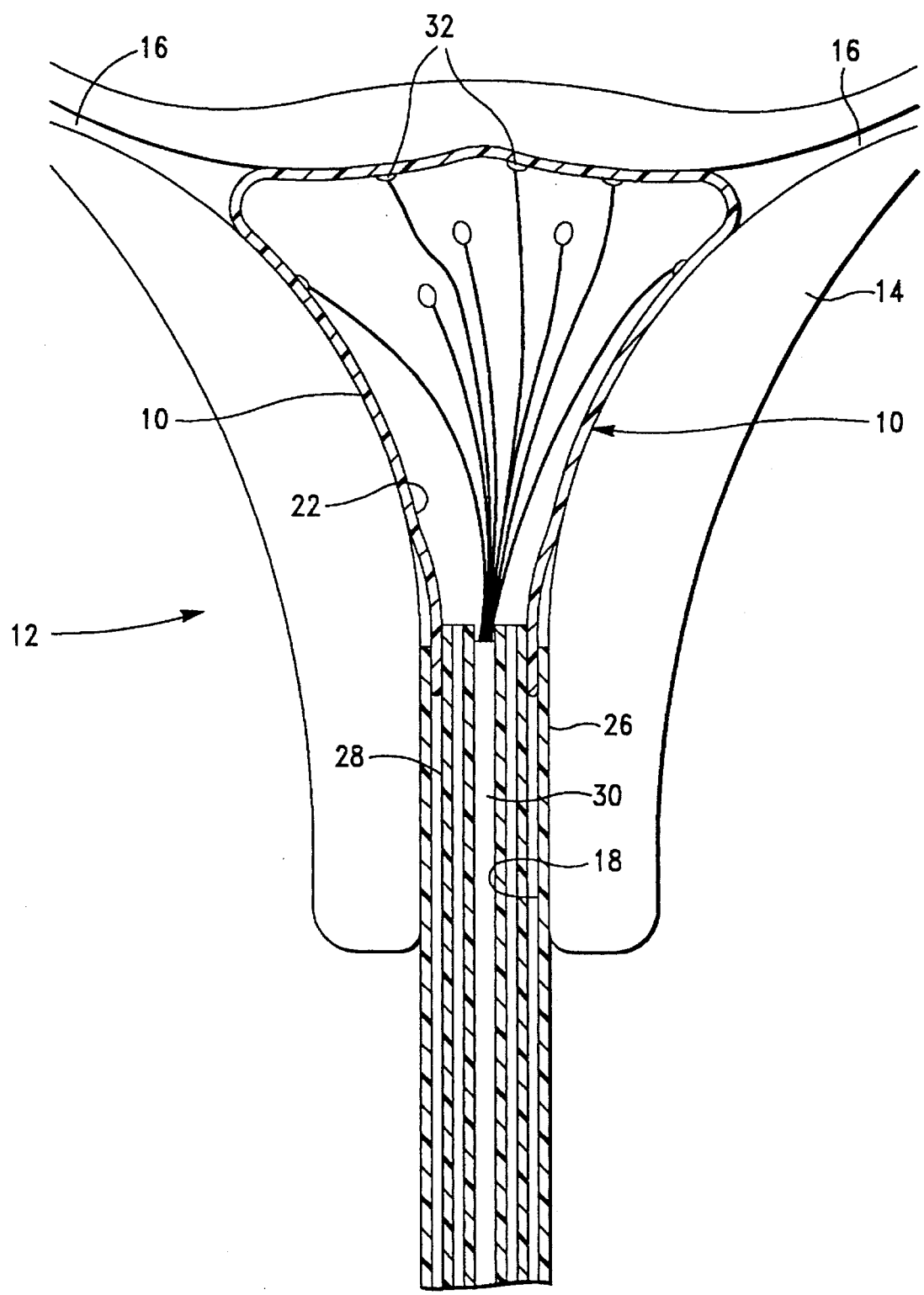
FIG. 1 is a cross-sectional representation of an electroconductive ablation balloon or bladder as an expandable member in an expanded format in place in a uterus.
Figure 2:
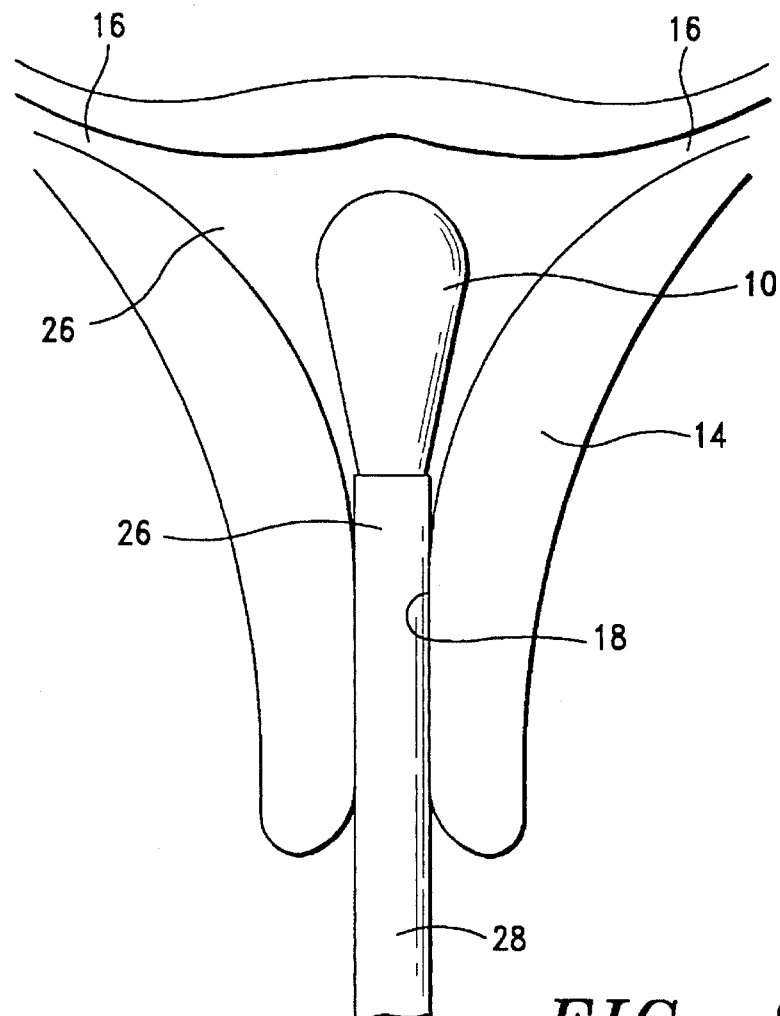
FIG. 2 is a representation of the apparatus of FIG. 1 in an unexpanded condition.

Referring now to the drawings, wherein like reference numerals designate identical or corresponding parts throughout the several views, and more particularly to FIG. 1 thereof, a cross-sectional representation of the invention utilizes an electroconductive ablation balloon or bladder 10 as the expandable member with FIG. 2 representing the same apparatus as FIG. 1 prior to inflation of the balloon element. The uterus 12 consists of myometrial tissue 14 surrounding the uterine cavity. The normal uterine cavity or envelope is a flat cavity having approximately the shape of an inverted triangle with the two upper corners communicating with the ovaries by way of the fallopian tubes 16 in the bottom corner opening into the cervical canal 18. The entire surface of the envelope includes the entrance of the fallopian tubes 16 and the cervical canal 18 which is covered with a thin layer of tissue known as uterine endometrium. The selective destruction of the endometrial cells is the goal of the improved method and apparatus disclosed in this present invention.

The monopolar electrode system developed in conjunction with FIG. 1 expands to conform to the endometrial surface to be treated and this in turn dilates and stretches the endometrium to reduce surface folds. Radio frequency electric current passes through the dilated endometrial surface for a time sufficient to destroy the endometrial cells by elevating the temperature of the endometrium to between 45° C. and 90° C. and preferably within 10 seconds. The temperature is maintained until the endometrial tissue is destroyed which is optimally accomplished by a temperature between 55° C. to 65° C. for up to 10 minutes.

The electric current passes through or along the surface of the expandable member and the interior of the expandable member is filled with an electrically non-conductive substance such as a fluid or gas. The expandable member can be any material or article which can be compressed or otherwise prepared in a small diameter configuration for insertion through the cervix and expanded or inflated after insertion to provide the dilation. This expandable member establishes direct electrical connection or capacitive coupling with the endometrium. A second electrical contact for the return electrode, also referred to as the ground electrode or indifferent electrode, can be a grounding plate or patch which contacts a large area of the patient's skin in order to complete the electrical circuit.

Electric current flowing through the tissue causes resistive heating. The power density diminishes with distance from the electrode as the reciprocal of the fourth power of the distance. Thus, any heat generated is focused in the endometrium and the immediately surrounding muscular tissue which in the particular case of the present invention is the portion of the myometrium 14 in contact with the lining. Because the myometrium 14 is highly vascularized, heat removal occurs rapidly. As a result of the vascularization and the rapid fall off of heating power with distance, the temperature of the endometrium 22 can be heated to a destructive temperature faster than the myometrium 14 and the rest of the uterus. Therefore, because of this temperature relationship, endometrial ablation can be safely accomplished as a simple medical procedure using local anesthesia. Furthermore, it can be a service made available at a fraction of the cost of prior art systems with less hazard than other endometrial ablations.

The inflatable balloon or bladder 10 is inserted into the uterine cavity 24 as shown in FIG. 2 by means of a catheter tube 26. The balloon 10 is secured to a fluid delivery tube 28. Inflation of the balloon occurs via the tube 28 with a gas or a non-conductive liquid so that the balloon extends and fills the uterine cavity conforming to the expanded surface as shown in FIG. 1. Portions of the balloon 10 extend into the entrance to the fallopian tubes 16 and extend along the entire endometrial surface 22 to the cervix 18. The balloon is attached to and forms a fluid-tight seal with the tube 28 which encloses an electrical cable 30 containing leads for the conductor as well as additional leads for sensors 32. A plurality of temperature sensors 32 are shown attached to the inner surface of the balloon. Alternatively, this lead configuration can be replaced by lead pairs for each sensor. The temperature sensors 32 are conventional thermistors or thermocouples and are positioned on zones of the balloon which will contact areas of the endometrial surface which are most sensitive to overheating. The temperature sensors can also be fiber optic temperature sensors. The fluid delivery tube 28 is connected to a source of gas or liquid through a conventional fluid control system which will be later illustrated in conjunction with FIG. 13.

Figure 3:
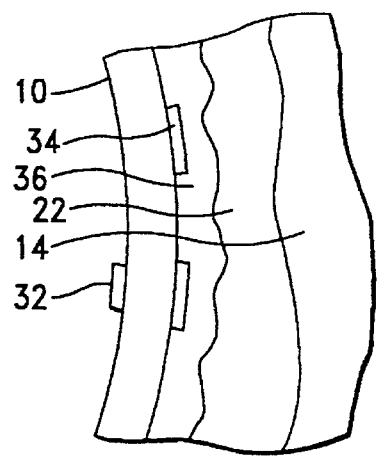
FIG. 3 is an enlarged cross-section illustrating the relationship between a small segment of the uterine endometrium and the expanded member.

The FIG. 3 is an enlarged cross-section illustrating the relationship between a small segment of uterine endometrium and the expandable balloon element of the FIG. 1. The endometrial lining 22, supported on the myometrium 14, is typically an irregular surface even after it is extended by the inflated balloon 10. Electrical contact between the conductive surface of the electrodes 34 and the endometrium 22 can be improved by covering the outer surface of the balloon with a conventional electroconductive solution, paste or gel 36 which is physiologically non-toxic and non-irritating. Suitable electroconductive media including the known types of gels and pastes used as surface coatings for defibrillators may be used. Examples of suitable conductive gels are carboxymethylcellulose gels made from aqueous electrolyte solutions such as physiological saline solutions and the like. The electroconductive solution, paste or gel enhances electrical contact between the balloon and the endometrium by filling the pores of the balloon surface and the irregularities in the endometrial surface. The electroconductive solution, paste, or gel can also be delivered to the space between the electrode balloon and the endometrium by utilizing the lumen 38 shown in FIG. 4b to administer the solution.

The expandable balloon or bladder 10 with its electrodes can be manufactured in a variety of ways. It can be an elastomeric polymer such as a natural or synthetic rubber made conductive by mixing the polymer with electroconductive particles such as carbon or conductive metal particles. It may, instead, be made conductive by a surface coating of electroconductive material such as an electroconductive gel, or a conductive metal coating on the outer or inner surface of the balloon or bladder wall. The electroconductive coating can be applied to organic polymer surfaces by conventional vapor deposition, electrical depositions, sputtering and the like.

One embodiment of the balloon comprises a thin, non-extensible polymer film such as a polyester or other flexible thermoplastic or thermosetting polymer film, for example, having a conductive metal coating on the outer and/or inner surface thereof. The film forms a non-extensible bladder having a shape and size, in its fully expanded form, which will extend the organ and effect contact with the endometrial lining to be destroyed. The inner surface of the non-extensible bladder can be coated with electroconductive material which will capacitively couple to the endometrium provided that the bladder wall thickness is less than approximately 0.25 mm.

The outer surface of the expandable member can be an open-cell, porous material such as a foam or similar caged network of material which can hold a quantity of the electroconductive solution, paste or gel required to secure satisfactory electrical contact with the opposed endometrial surface. The surface can be coated with or impregnated with the electroconductive substance, or it can be administered through the lumen 38 shown in 4b.

FIG. 4 illustrates an embodiment using a balloon 40 with a plurality of surface segments 42 as the expandable bladder member. Each of the surface segments has a conductive surface and a temperature sensor. In this particular embodiment, the balloon has a segmented electrode coating of electroconductive metal on either the inner or the outer surface to permit controlled delivery of power to each segment. Each segment 42 is electrically connected through conventional leads to a power source (not shown in FIG. 4). Each conductive segment 42 also has a thermistor 44 which is connected through conventional leads to a switch matrix. FIG. 4b illustrates a top view of the bladder electrode 39 and particularly features a lumen 38 extending through the center of the bladder electrode. The lumen allows for light and viewing guides to be inserted through the center of the bladder. In other words, there is an inner lumen tube 38 attached to the center of the flat film.

Figure 5:
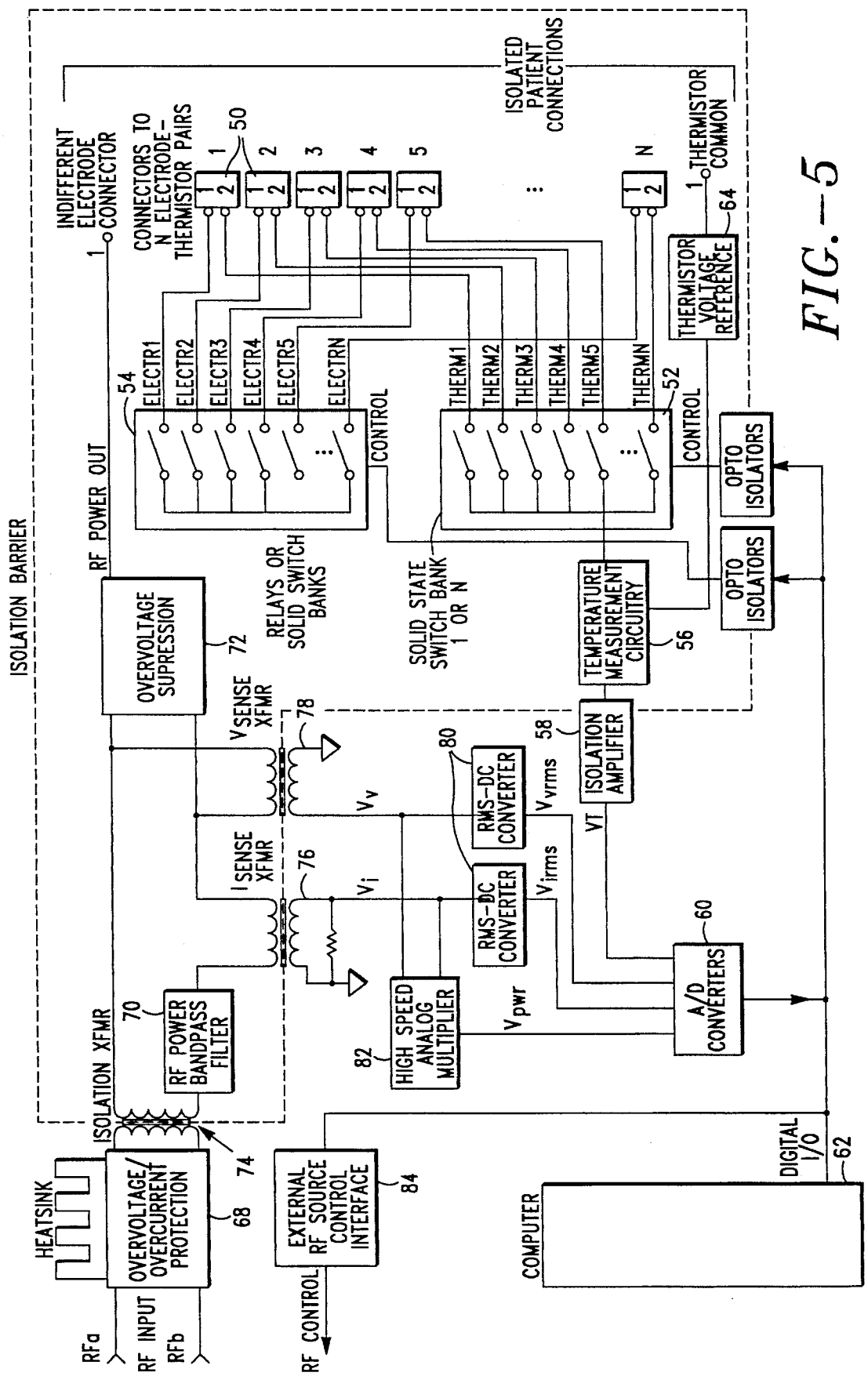
FIG. 5 is a schematic representation of the power control system for the multi-segment element shown in FIG. 4.

FIG. 5 is a schematic representation of the power source controller and the switch matrix for the multi-segment balloon discussed above in conjunction with, for example, FIG. 4. The electrical leads connect to the electro-thermistor pairs of the bladder of FIG. 4 by way of connectors 50 as shown in FIG. 5. The thermistor leads are connected to the matrix switch bank 52 and the electrode leads are connected to the switch bank 54. Each thermistor 44 (FIG. 4a) is sampled by means of the temperature measurement circuitry 56 and the isolation amplifier 58 before being converted in the converter 60 and fed to the computer 62. The temperature measurement circuitry compares the measured temperature with a thermistor reference voltage supplied by a voltage reference 64. The electrode switch 54 is controlled in response to the output of the computer 62 by means of the opto-isolators 66. Input power from the RF input passes through the overvoltage and overcurrent protector 68 and is filtered by the bandpass filter 70 before being subjected to overvoltage suppression by the suppression unit 72. The voltage is isolated by means of the transformers 74, 76 and 78 with the transformer voltages $V_i$ and $V_v$ from the transformers 76 and 78 being converted by the RMS-DC converters 80 into an RMS voltage to be fed to the converters 60. Prior to conversion, the signals $V_i$ and $V_v$ are also fed to a high-speed analog multiplier 82. RF control from computer 62 is provided through interface 84.

Figure 6:
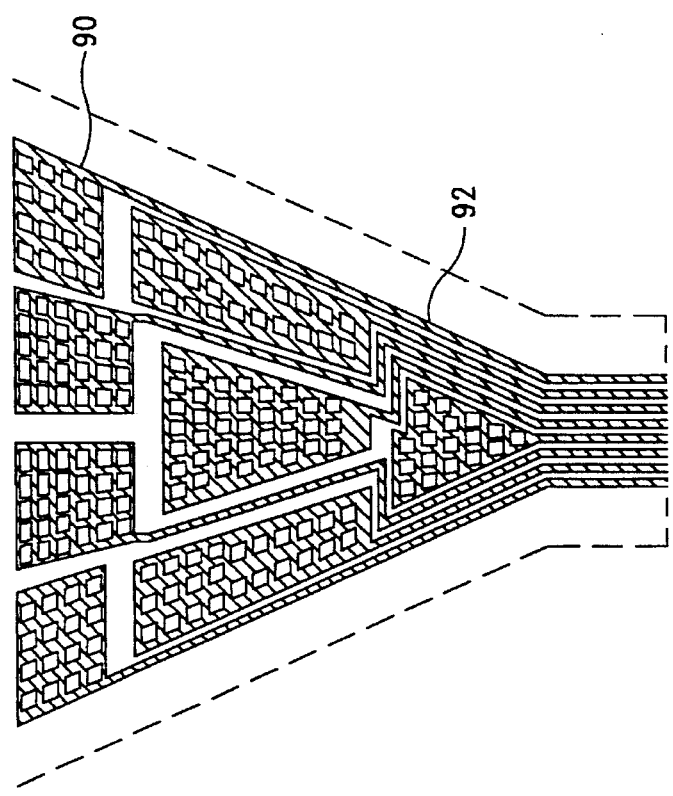
FIG. 6 illustrates an embodiment of the multi-segment element having perforated electrodes with illustrated power traces on the outside surface of the expandable member.

A variation of the electrode structure of FIG. 4 is shown in FIG. 6 wherein there are perforated electrodes 90 illustrated with their leads in the form of power traces 92. This particular electrode bladder of FIG. 6 is shown with the perforated electrodes 90 on the exterior of the bladder.

Figure 7:
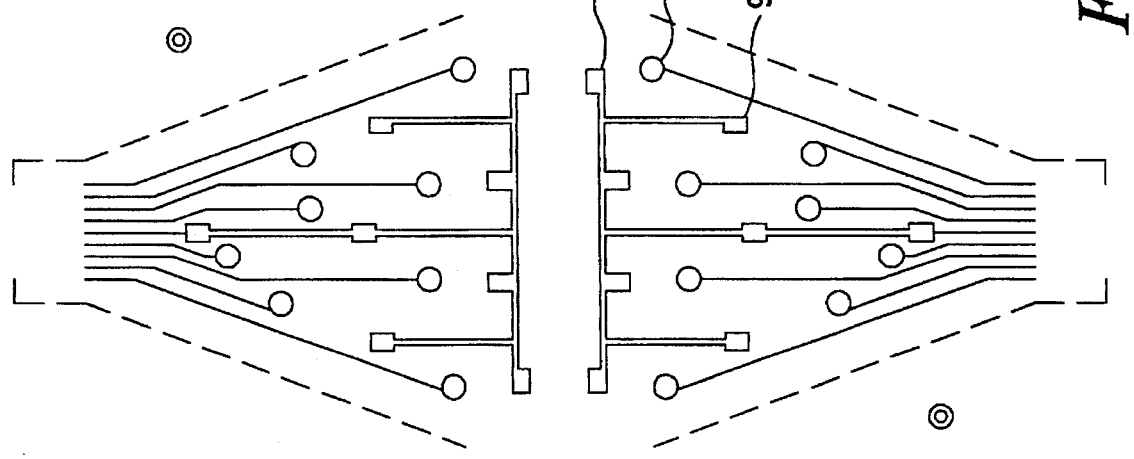
FIG. 7 illustrates thermistor traces and circular wiring jumper mounting pads on the interior of the expandable member.

FIG. 7 illustrates thermistor common-side traces 94 on the interior of the bladder with circular wiring jumping pads 96 with mounting sites 98 serving as the base for the thermistors. The common-side traces provide power for both the electrodes and the associated thermistor. FIG. 7 illustrates both interior sides of the bladder.

Figure 8A:
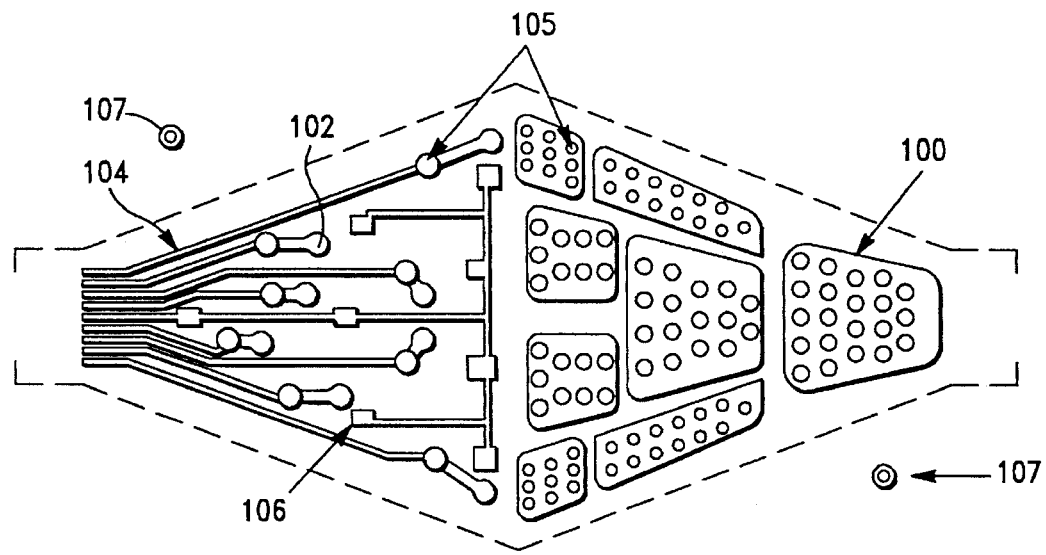
FIGS. 8a and 8b illustrates the double-sided electrode/thermistor traces on the respective inside and outside portions of the expandable member of FIGS. 6 and 7.

FIG. 8a illustrates both the outside and the inside of a double-sided electrode with thermistor traces having perforated electrodes 100 on the outside and thermistor wiring pads 102 and electrode power leads in the form of traces 104 as well as thermistor mounting sites 106 on the inside. The connection between the inside and outside of the bladder is achieved by means of the via hole 105 in the FIG. 8a. Alignment fiduciaries 107 are shown for aligning the two halves of the bladder. The FIG. 8a embodiment corresponds to a combination of the inside illustration of the power traces and the bonding surfaces from FIG. 7 along with the perforated electrode of FIG. 6 with the exception that FIG. 8a has the power traces on the inside surface whereas the embodiment of FIG. 6 has the power traces for the perforated electrodes on the outside surface.

Figure 8B:
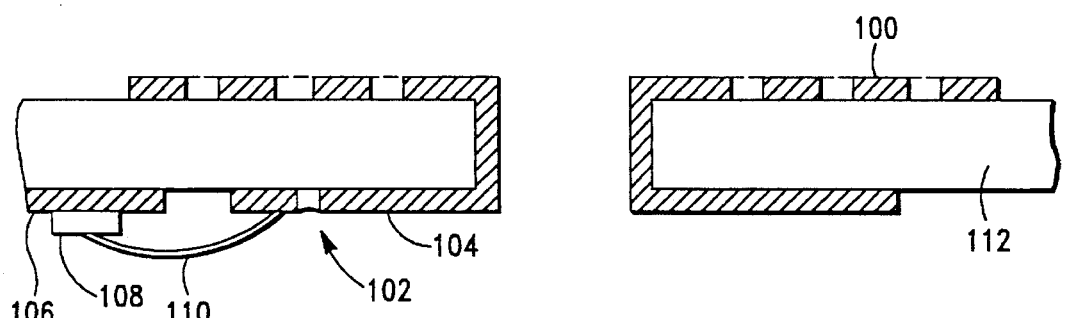

FIG. 8b specifically shows a cross-sectional view of the bladder with the electrode 100 on the top or outside surface and the power traces 104 and thermistor wiring pads 102 and mounting sites 106 on the lower or inside surface. FIG. 8b also illustrates the mounting of the thermistor 108 on the mounting site 106 with a connection between the power trace 104 and the thermistor 108 being made by the thermistor lead 110. FIG. 8b clearly illustrates that all except one of the holes in the perforated electrode 100 have a depth which reaches to the insulating substrate or bladder 112. The via hole 105 extends through the entirety of the bladder as an electrical connection between the perforated electrode 100 and the power trace 104 on the bottom or inside surface.

Each of the views of FIGS. 6, 7 and 8, whether on the inside or the outside must be understood to represent only two surfaces of a bladder which must necessarily have four surfaces. The bladder, prior to inflation, can be envisioned as triangular with two outside triangular surfaces (top and bottom) and two inside triangular surfaces prior to inflation.

Figure 9:
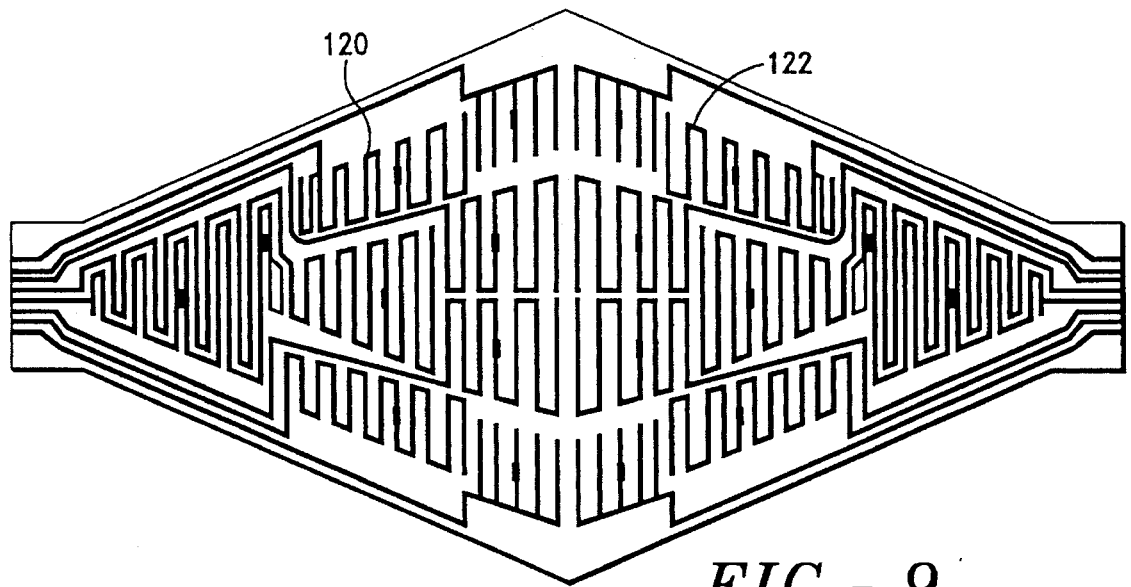
FIG. 9 illustrates an embodiment utilizing flat metallized stock material to be adhesively bonded to the expandable member with the material being arranged in a serpentine configuration.

A further variation of the electrode structure is shown in FIG. 9 which illustrates a flat metallized stock material adhesively bonded as electrodes 120 and 122 to the outside of both the top and the bottom of the bladder. The electrodes, which are metallized and adhesively bonded, form a serpentine electrode pattern in order to promote uniform application of RF energy to provide uniform heating of the area.

Figure 10A:
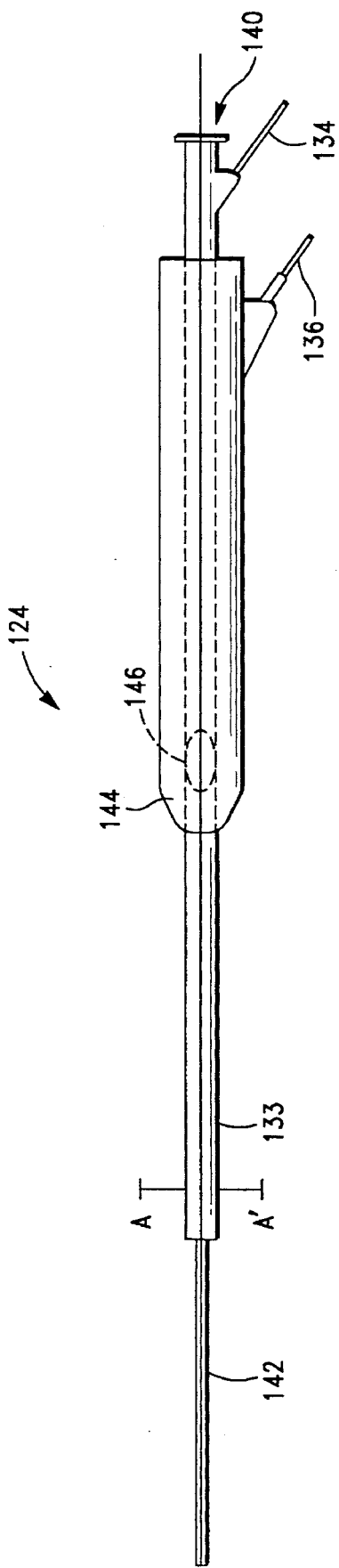
FIGS. 10a–b show the bladder device for delivering the expandable member to the uterus.
Figure 10B:
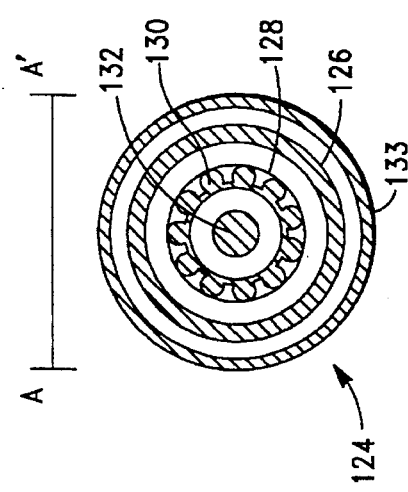

FIGS. 10a and 10b illustrate the bladder application device which is used to insert the bladder. FIG. 10a is a side view of the application device 124. FIG. 10b is a cross section through the device 124 along the line A—A in FIG. 10a. FIG. 10b illustrates the device 124 with a fluid delivery tube 126 secured to the bladder (not shown). A shrink wrap 128 covers the wiring leads 130. A fiber bundle 132 is located in the center of the applicator which would be connected through the lumen 38 illustrated in FIG. 4b, for example. FIG. 10b further shows a catheter sleeve 133. The applicator device 124 has an inflation inlet 134 and an electrode wiring insertion port 136 as well as the optical viewing fiber inlet 140 connected to a lumen such as the lumen 38 shown in FIG. 4b. Retraction of the catheter sleeve 133 relative to the bladder 142 is achieved using the alignment guide and sheath retraction knob 144 acting in conjunction with a thumb detent 146. The applicator of FIG. 10a shows the bladder 142 in an extended but unexpanded position.

The FIGS. 11a–c illustrate the bladder device of FIG. 10 in a retracted position with FIGS. 11b and 11a being taken at the cross sections titled A–A' and B–B' respectively. FIG. 11a illustrates the position of the deflated bladder 142 with respect to the main tube in the retracted position at line B–B'. The remaining features of the applicator 124 remain as indicated with respect to FIG. 10.

Figure 12:
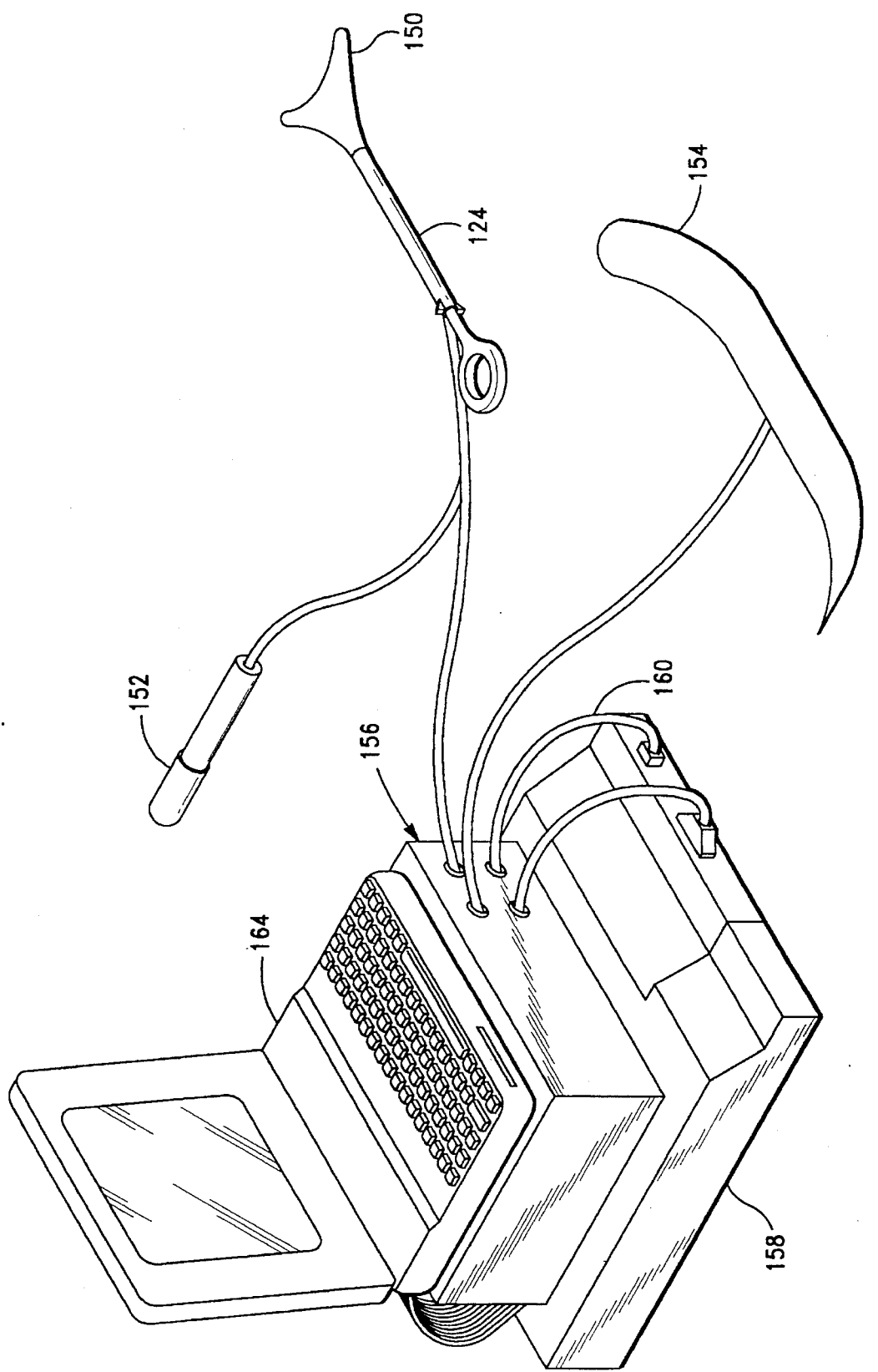
FIG. 12 schematically represents the connection of the bladder device to the power generation source and testing structure.

An illustration of the connection of the application device 124 and the electrode balloon 150 in accordance with any one of the embodiments of the FIGS. 6–9 is illustrated in FIG. 12. An inflation pump 152 provides the medium for the expansion of the balloon 150 while the electrode belt 154 provides the reference electrode for connection to the power source controller 156 which may be configured as described with respect to FIG. 5. RF generator 158 serves as the RF input power for the controller 156 by means of electrosurgical interface cables 160. The controller 156 includes an interface 162 for connecting the controller 156 to the portable computer 164.

Once the device 124 and the controller 156 are connected, the RF electrodes are separately, independently and sequentially energized with thermistor temperature feedback to bring the endometrial temperature up to a desired level. The system accomplishes this in an automated manner using the RF output from a conventional electrosurgical power supply 158. As discussed previously, the electrodes may have a variety of specific configurations and heating is concentrated in the endometrium near the surfaces of the electrodes. Various electrode configurations provide uniform RF energy distribution to produce uniform heating. An example of the concentration of the heat over the entire surface of the electrode is available from the embodiment wherein holes are provided through the electrode as shown in FIGS. 6 and 8. Uniform heating is also obtained by extending the electrodes in a pattern of lines such as the serpentine pattern structure of FIG. 9.

As a result of these kinds of constructions, the treatment method of the present invention as well as the electrode elements provide an increased current density as a function of the "electrode edge length" available for tissue heating. Furthermore, as discussed previously, the electrodes can be on the outer surface of the bladder while the power traces, thermistors, and thermistor leads can be on the inner surface of the bladder. Instead the thermistors can be secured to the electrodes.

In the embodiments of FIGS. 6–9, the various electrode patterns feature common power traces for both the electrodes and the associated thermistors. That is, one power lead provides the power for an individual electrode as well as its associated thermistor thereby saving in the construction of the bladder electrodes by reducing the number of required thermistor leads. In such embodiments, each electrode has a corresponding thermistor lead in common with the RF power lead. The second leads from all thermistors are then connected together to form a thermistor common as shown for example in the FIGS. 7 and 8a. This arrangement provides the advantage that it only requires N+1 leads to drive an ablation balloon with N electrodes and N thermistors. Because of this construction, however, the temperature measurement circuitry 56 of FIG. 5 has additional requirements beyond the construction with a separate power lead for each thermistor and for each individual electrode. The construction with separate power leads for the electrodes and the thermistor are well known and any one of a variety of temperature measurements schemes for individual electrodes could be utilized.

Figure 13:
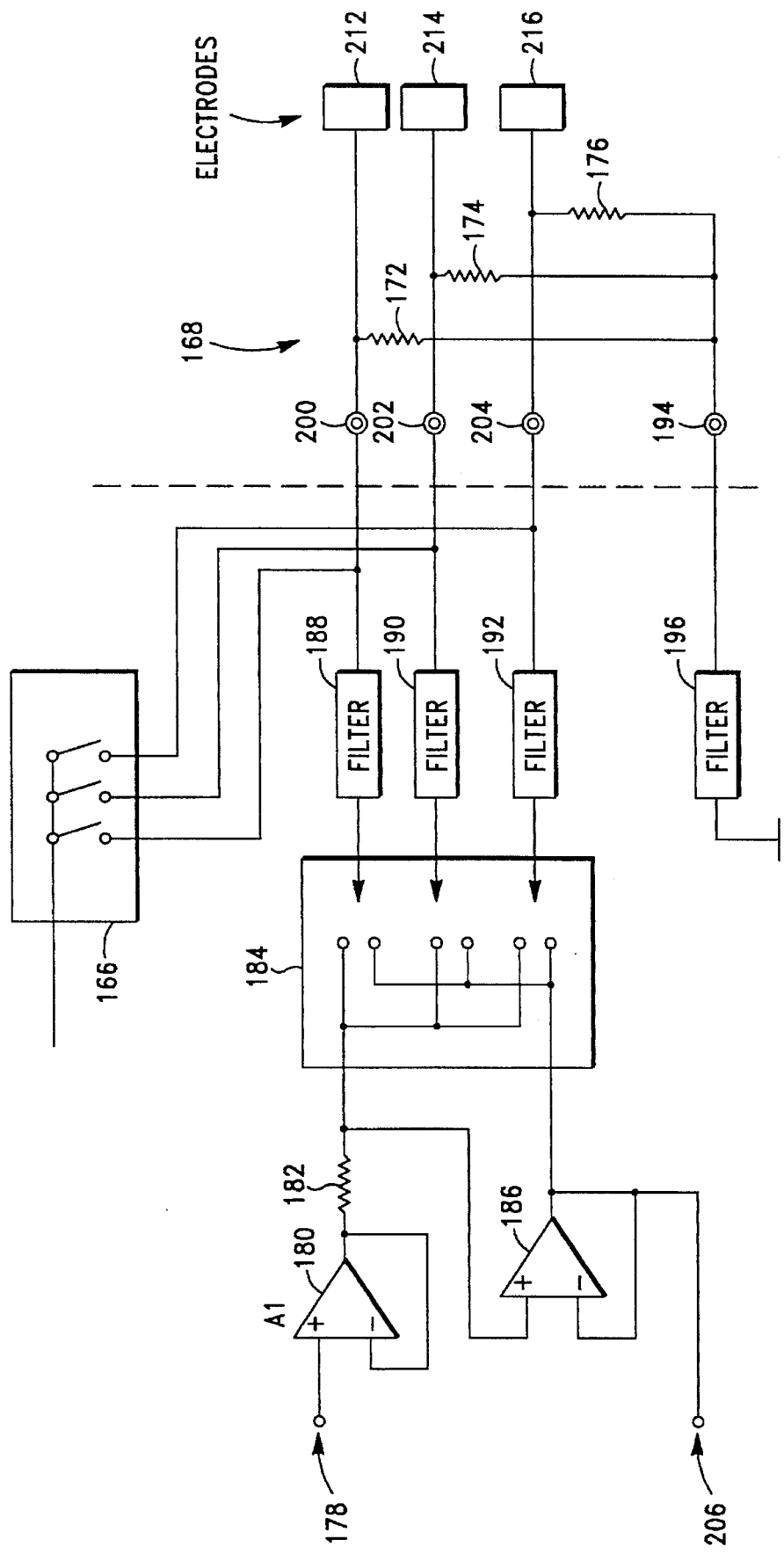
FIG. 13 is a schematic of an embodiment of the temperature measurement circuitry of FIG. 5.

The specialized requirements brought about by using a common power lead for each electrode and each thermistor are met by the embodiment shown in the FIG. 13. In FIG. 13, RF power is selectively applied through switch matrix 166 so that it can be applied to selected electrodes. The electrode/thermistor circuitry is represented on the right hand side of FIG. 13 generally as 168 with a particular example being given by three electrodes and three thermistors represented by resistors 172, 174 and 176. A reference voltage Vref indicated by reference numeral 178 is buffered by an operational amplifier follower 180 and passes through resistor 182 ($R_B$) before entering the measurement switch matrix 184. The output of resistor 182 is buffered by operational amplifier follower 186. Outputs of the measurement switch matrix 184 are fed through the filters 188, 190 and 192 which represent low pass filters which block high frequency RF but pass DC and very low frequency voltages.

The balloon thermistor common lead 194 passes through the filter 196 to ground.

During operation, RF power is applied to a particular desired electrode or electrodes by operations of the RF power switch matrix 166. Measurement of thermistor resistance 172, 174 or 176 is independent of the particular electrodes connected to the RF power. In order to provide a measurement of resistor 172 (RT1), measurement switch matrix 184 is set up to connect lead 200 to the right hand side of resistor 182 while all other leads are set to be connected to the output of the operational amplifier follower 186. This particular set up and arrangement forces the voltage $V_T$ indicated by reference numeral 206 to be equal to $V_{REF}$ RT1/($R_B$+RT1). Therefore this allows the measurement of RT1 due to the known value of $R_B$ and $V_{REF}$. Because the other leads 202, 204 from the circuitry 168 are held at the same voltage by the follower 186, there are no voltage differences between any of these leads and therefore no current will flow between them.

This lack of a current between leads is extremely important because the tissue which contacts the electrodes causes an effective shunt current path that would, in the absence of the circuitry of FIG. 13, affect the measured voltage $V_T$ 206.

Figure 14:
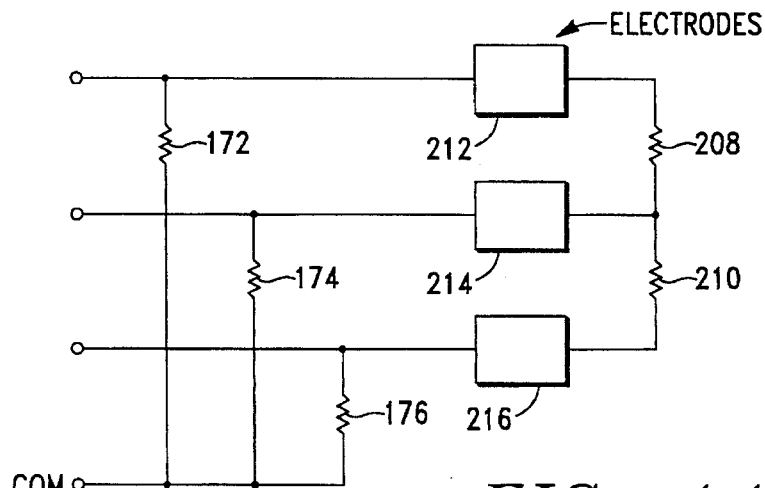
FIG. 14 is an equivalent of FIG. 13 showing effective tissue shunting.

This effective shunting by the tissue is illustrated by the equivalent circuit of FIG. 14 which shows effective tissue resistances 208 and 210 connected between electrodes 212, 214 and 216.

The delivery of power can be improved by utilizing a bipolar construction. The use of unipolar power delivery of the type illustrated in FIGS. 5 and 13 necessarily implies current paths between each one of the bladder electrodes 50 (FIG. 5) and the return electrode 154 (FIG. 12). Thus the resistance heating which occurs can depend on the return path which in turn depends upon the placement of the return electrode 154 on the patient. Typically the return electrode 154 is a large patch placed on the back of the patient thus determining what is essentially an unknown series of return paths for the current. In some instances a monopolar operation is satisfactory but improved control can be achieved in many cases if a bipolar operation is utilized. When a bipolar operation occurs, the flow of the current return is a path between selected pairs of the electrodes. A switching arrangement to be described determines such pairs of electrodes or combinations of electrodes between which the current flows in the return path.

In specific instances, it would be more precise to provide a more even heating of a uterus or other body organ if the electrode could have a controlled return path for the current. In such instances, if particular pairs of electrodes were chosen in a bipolar arrangement to receive RF energy, the return path could be controlled selectively by a physician who is performing a visual inspection by means of an x-ray, ultrasound, or other detection device. This precise control can only be afforded in a bipolar arrangement. Obviously, in some instances the precise control is either not necessary or treatment can best be performed in a monopolar arrangement.

Figure 15:
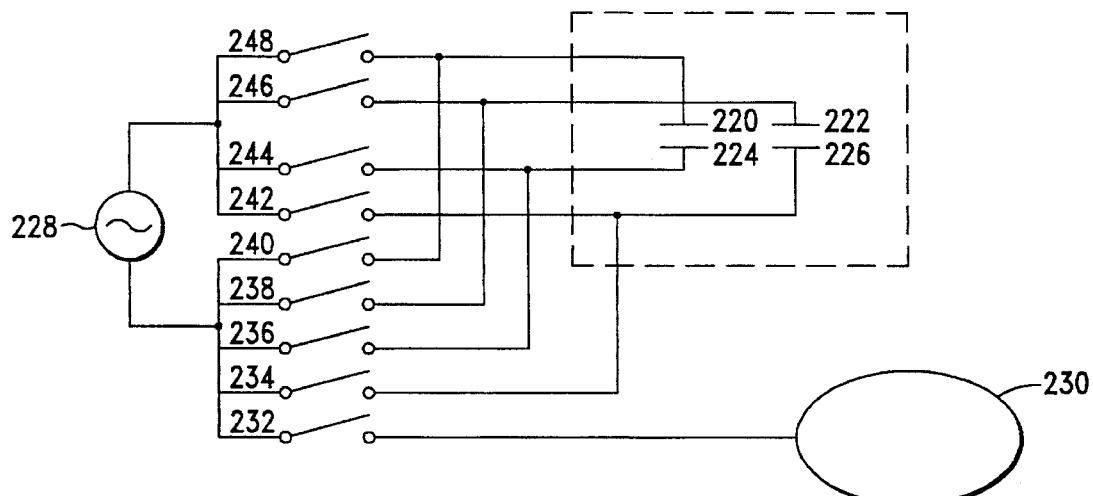
FIG. 15 is a schematic of a selectable bipolar/monopolar RF energy delivery system for a plurality of electrodes or electrode segments.

The device of FIG. 15 provides an apparatus for both bipolar and monopolar application of RF energy with the choice of either bipolar or monopolar being made by control of the switches. Furthermore, not only are the modes selectable by controlling the switches but also within the bipolar mode, for instance, the switches allow for the selective application of RF energy to various combinations of electrodes.

FIG. 15 illustrates the use of four electrodes 220, 222, 224 and 226 and a voltage source 228 with the same patient grounding pad or patch or return electrode 230 as in, for example the FIG. 5 unipolar arrangement. The essence of the FIG. 15 monopolar/bipolar switching arrangement is that the physician or operator has the ability to provide either monopolar or bipolar operation. When switch 232 is closed and the switches 234, 236, 238 and 240 remain open, the device functions essentially the same as the FIG. 5 embodiment. That is, it provides monopolar operation. On the other hand, if the switch 232 is opened and if pairs of switches, with one of the pair being selected from the switches 242, 244, 246 and 248 and the other being selected from switches 234, 236, 238 and 240, are operated in proper conjunction, the electrodes 220, 222, 224 and 226 will provide a bipolar operation. As an example, if switch 248 is closed as well as switch 236, then the current will pass from electrode 220 to electrode 224. In a similar manner, if switch 246 is closed as well as switch 234, there will be a bipolar operation with current flowing between electrodes 222 and 226. Clearly bipolar operation is not limited to these 220–224 and 222–226 pair couplings. If switch 248 and switch 238 are closed there will be bipolar operation between the electrodes 220 and 222.

Figure 16:
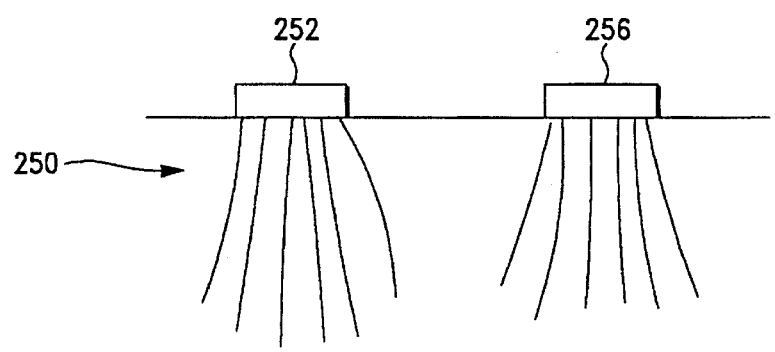
FIG. 16 shows electric field lines outside a monopolar electrode.
Figure 17:
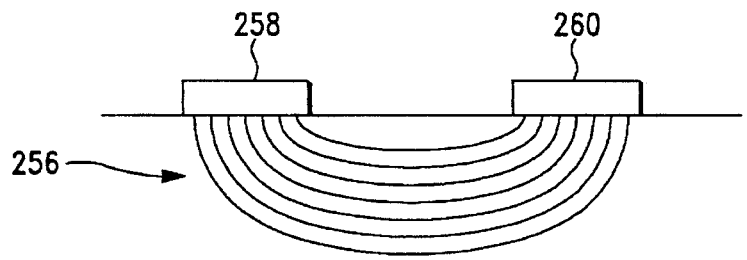
FIG. 17 shows electric field lines outside a bipolar electrode pair.

The difference in operation between monopolar and bipolar performance can be seen from a comparison of FIGS. 16 and 17. The FIG. 16 shows a structure or a balloon 250 having 2 electrodes, 252 and 254 which operate in the monopolar condition. It can be seen that the electric field lines proceed between each one of the electrodes 252 and 253 and a return electrode (not shown) comprising a ground plate or patch such as the return electrode 230 of FIG. 15 placed on the outside of a patient. In contrast, a bipolar operation is shown in FIG. 17. The balloon 256 includes electrodes 258 and 260. The electric field lines proceed between the two electrodes. With a bipolar electrode, the current paths are more easily controllable by appropriate placement and activation of the electrodes whereas the field lines in FIG. 16 in monopolar operation depend on the placement of not only the electrodes 252, 254 but also on the placement of the grounding pad 230 and on the physical structure of the individual patients.

Figure 18:
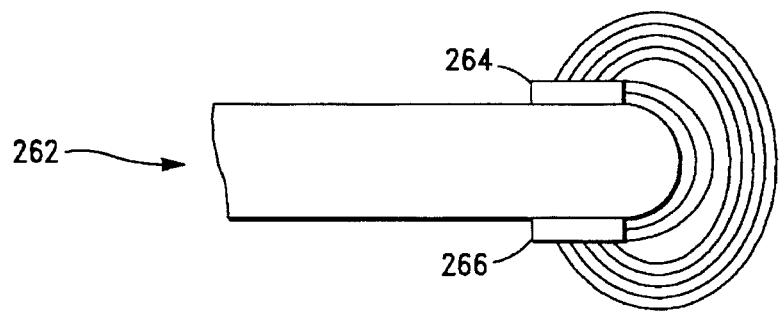
FIG. 18 shows how bipolar energy may be directed to flow around the edges of the balloon.

The ability to control field lines, and therefore the heated area, utilizing bipolar operation is exemplified in FIG. 18 wherein there is a balloon 262 having electrodes 264 and 266 with the field lines passing through the patient in such a way that effectively the bipolar energy may be directed to flow around the edges of the balloon 262 in order to insure complete heating of an area. The bipolar arrangement allows various pairs of electrodes to be picked in order to heat uneven or rather asymmetrical areas within individual patients in which the balloons are inserted or within specialized needs for certain tissue destruction. That is, any unusual features within an area to be heated may be taken into account in a bipolar operation by selection of different pairs of electrodes for energization utilizing the circuitry of FIG. 15. As an example, these areas may be known from a doctor's observation either before or during an ablation or heating procedure. The visual inspection may be aided by one of a number of imaging techniques.

The embodiment of FIG. 15 not only provides a choice between monopolar and bipolar operation but also provides flexibility within the bipolar operation so that any pair or any combination of pairs of electrodes may be utilized together. Obviously, if both switches 248 and 240 were closed nothing would occur because there would be a short circuit.

Various techniques may be employed in manufacturing the device of the invention. In one embodiment the bladder and electrodes are constructed in accordance with a method wherein a double-sided thin flat film is used which is plated on both sides. A mask is provided for an electrode pattern on the one side. Using lithographic techniques, unmasked areas are etched away leaving the desired pattern. Then a mask is deposited for the conductors which lead to the temperature sensing elements on a second side to provide conductors using lithographic techniques.

The thermistors 44 (FIG. 4a) are provided using surface mounting techniques and the attached inner lumen is provided at the center of the flat film in a manner described in greater detail below. The balloon is then folded and sealed to the main tube 126 (FIG. 10b) at the proximal end of the tube. Subsequently, conductors are brought to the outside of the main tube to the end of the device near the handle of the applicator. The outer sheath 133 is slidably received over the conductor as shown in FIG. 10b. Finally, the handle of the applicator of FIG. 10 or FIG. 11 is assembled.

Other forms of providing an electrode balloon may be used such as utilizing a blow molded preform or the formation of the balloon with copper on kapton conductive elements on the surface of a compliant balloon. Furthermore, this balloon may be formed as a "sock" to fit over an inner latex balloon with the sock being a compliant device. Other anticipated forms of an electrode balloon structure include the use of the plated or etched wiring all the way from the balloon itself down to the handle.

Figure 19:
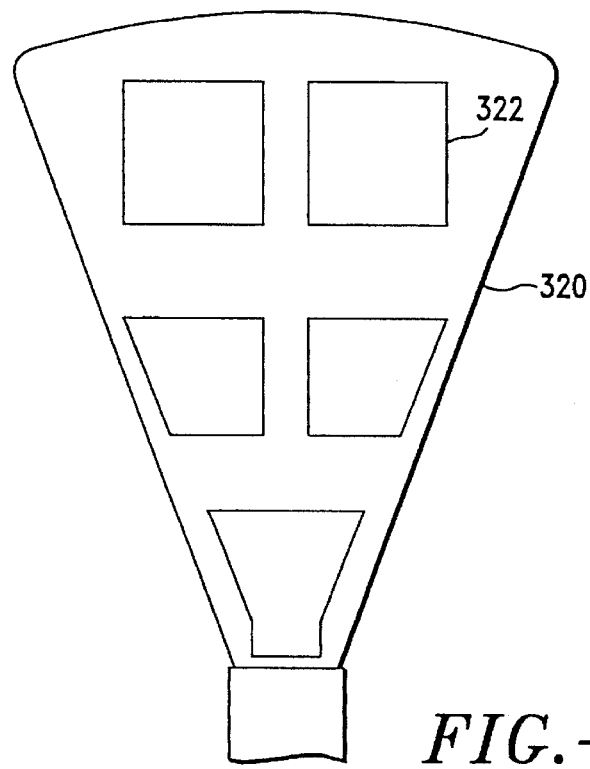
FIG. 19 is a side view of one embodiment of an ablation balloon in accordance with the invention.

One type of bladder or balloon found to work particularly well is a balloon made of a stretchable material which can accommodate various shapes and sizes of uteri. Clearly the use of an elastic material requires specific manufacturing techniques. Various embodiments of such a device and methods of manufacturing the devices will now be discussed in detail with reference to FIGS. 19 to 39 below. The device comprises an expandable bladder having a substantially equilateral triangular shape with rounded corners as illustrated in FIG. 19. The bladder 320 can be made of any suitable expandable material capable of withstanding the ablation temperatures which are typically less than 90° C. and generally lie in the range of 45° C. to 90° C. and more particularly in the range of 55° C. to 85° C. Clearly the bladder can be made of a pleated material; however the discussion which follows is directed specifically to a stretchable material. Silicone rubber has been found to work particularly well for the body of the bladder 320.

At least one electrode is formed on the bladder 320. In the embodiment illustrated in FIG. 19, a plurality of electrodes 322 are formed on the surface of the bladder 320.

The electrodes may be formed by a variety of techniques. Metal could, for example, be deposited through a mask onto the polymer substrate. This could be achieved by a sputtering process, an ion beam assisted deposition process or an electroplating technique.

Alternatively, the electrodes could be incorporated into the substrate. In this technique a conductive powder could, for instance, be incorporated into the polymer substrate of the balloon 320 during the forming of the substrate.

A third technique which has been found to work particularly well involves securing plates which constitute discrete conductive islands onto the substrate. This can be achieved in a number of ways, three of which are described below.

Figure 20:
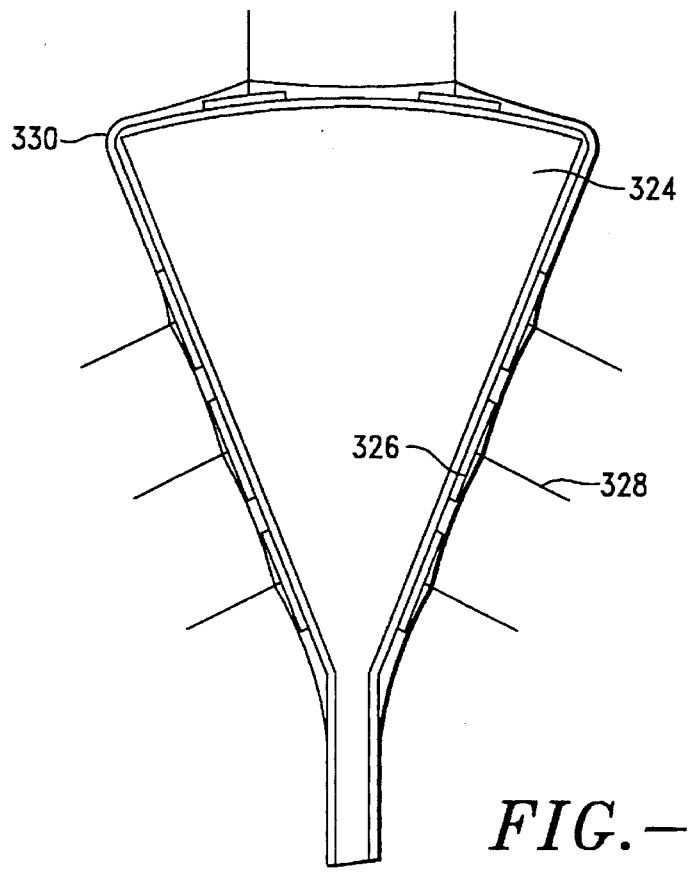
FIG. 20 is a sectional side view of one embodiment of an ablation device in accordance with the invention.

In the first of the three techniques, illustrated in FIG. 20, a dip molding process is used. In this process, a mandrel 324 is provided which has the appropriate shape desired for the bladder. Electrodes 326 are secured to the mandrel, for example by means of an adhesive. The electrodes 326 are provided with electrode leads 328. The mandrel 324 is then coated with an uncured elastomer emulsion, for example by dipping it into an uncured emulsion which cures around the mandrel 324 and the electrodes 326 to form a bladder supporting the electrodes 326. A suitable emulsion would be a silicone or polysiloxane rubber emulsion having a heat resistance of 200° C. to 300° C. The mandrel 324 typically comprises a collapsible structure which is collapsed once the emulsion has cured. The silicone rubber layer 330 is then peeled off the mandrel and inverted to form a bladder with external electrodes and internal electrode leads. The emulsion forms a seal around the electrode leads 328 to provide an airtight bladder.

In another technique illustrated in FIG. 21 a planar piece of expandable substrate 340 is formed by depositing an uncured emulsion onto a planar surface. Once cured, the substrate 340 is peeled off the planar surface and folded along a center line 342. The abutting layers are then joined along the lines 344 and 346 to form a bladder similar to the one in FIG. 20. The edges 344 and 346 are typically connected to one another by means of an adhesive. In this embodiment holes are pierced through the substrate 340 for electrode leads. Electrodes are secured to the one surface of the substrate 340 by means of an adhesive, and the electrode leads are passed through the holes formed in the substrate to extend out through an opening in the bladder which is defined by the unsealed sides 347.

Clearly commercially available stretchable planar material can be used instead of manufacturing it by forming it on a former.

Another method, and the one preferred, is illustrated in FIG. 22. In this embodiment the substrate is again formed on a substantially flat surface. However, in this case the electrodes are not subsequently secured to the substrate; they are embedded in the substrate during the curing process. The electrodes 350 are secured to a planar base 352 in one of a variety of techniques discussed in greater detail below. Temperature sensors 354 are placed on at least some of the electrodes 350. They may be secured to their electrodes, for example by means of an adhesive. Leads 356 extend from the electrodes 350 and temperature sensors 354 but are indicated by a single line for each electrode-temperature sensor pair. The emulsion, for example a silicone rubber emulsion, is then spread over the temperature sensors 354, electrodes 350 and base 352 to embed the temperature sensors 354 and electrodes 350 in the uncured emulsion. This secures the temperature sensors 354 against the electrodes and forms seals around the leads 356. Once the emulsion has cured the resultant silicone rubber layer with the temperature sensors 354 and electrodes 350 secured thereto is peeled off the base 352.

Figure 23:
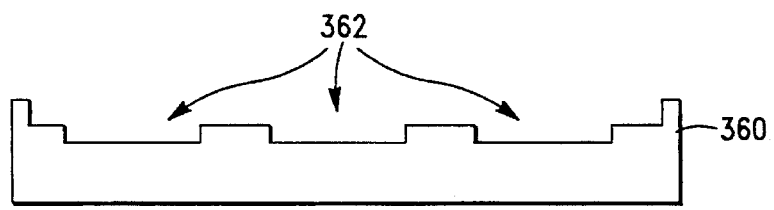
FIG. 23 is a sectional side view of one embodiment of a support base for use in manufacturing an ablation balloon of the invention.

Instead of using a planar base 352, a base 360 may be used as illustrated in FIG. 23. The base 360 is provided with depressions 362 which are milled into the base 360 to accommodate the electrodes (not shown). Typically the base is made of aluminum. By using depressions in the base 360 a bladder can be formed in which the electrodes extend outwardly from the surface of the bladder. In the embodiments illustrated in FIGS. 22 and 23, the substrate is folded and sealed in a manner similar to that described with respect to FIG. 21. The sealing of the edges may again be achieved by means of an adhesive or by using ultrasonic welding or a heat seal. If a silicone rubber is used as the substrate material, an adhesive is typically used, the technique being described in greater detail below.

Figure 24:
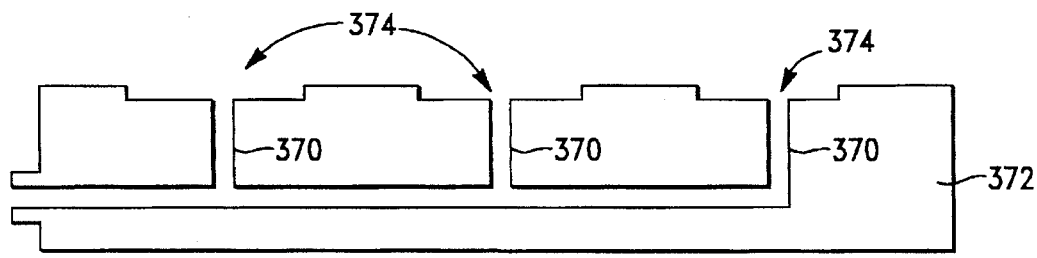
FIG. 24 is a sectional side view of another embodiment of a support base.

In order to retain the electrodes relative to the base while the substrate material is spread over the base and electrodes and while the material is curing, a vacuum technique or adhesive may be used. The vacuum technique is illustrated in FIG. 24. Channels 370 are provided in the base 372 in flow communication with the various electrode zones 374. The channels 370 are connected to a vacuum source (not shown). Electrodes (not shown) placed in the zones 374 may thus be held in place by a suction process.

An alternative technique is that illustrated in FIG. 25 in which a mechanical jig 380 is placed over the base 382. The jig 380 includes pins 384 extending outwardly from surface of the jig 380 and aligned with the electrodes 386 on the base 382. By securing the jig 380 relative to the base 382, the pins 384 mechanically hold the electrodes in place.

Figure 26:
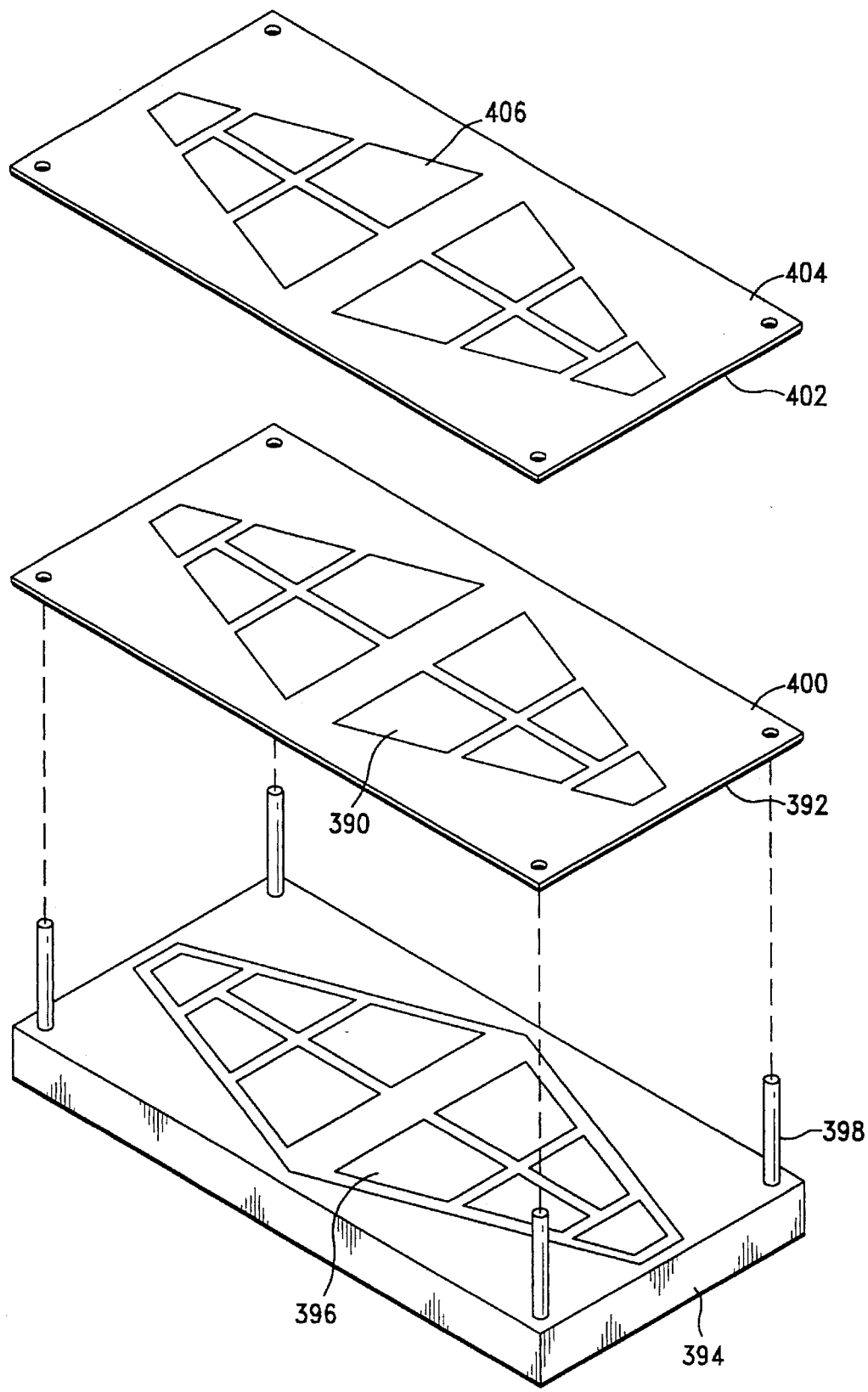
FIG. 26 is an isometric view of a support base showing a part of the manufacturing process.
Figure 27:
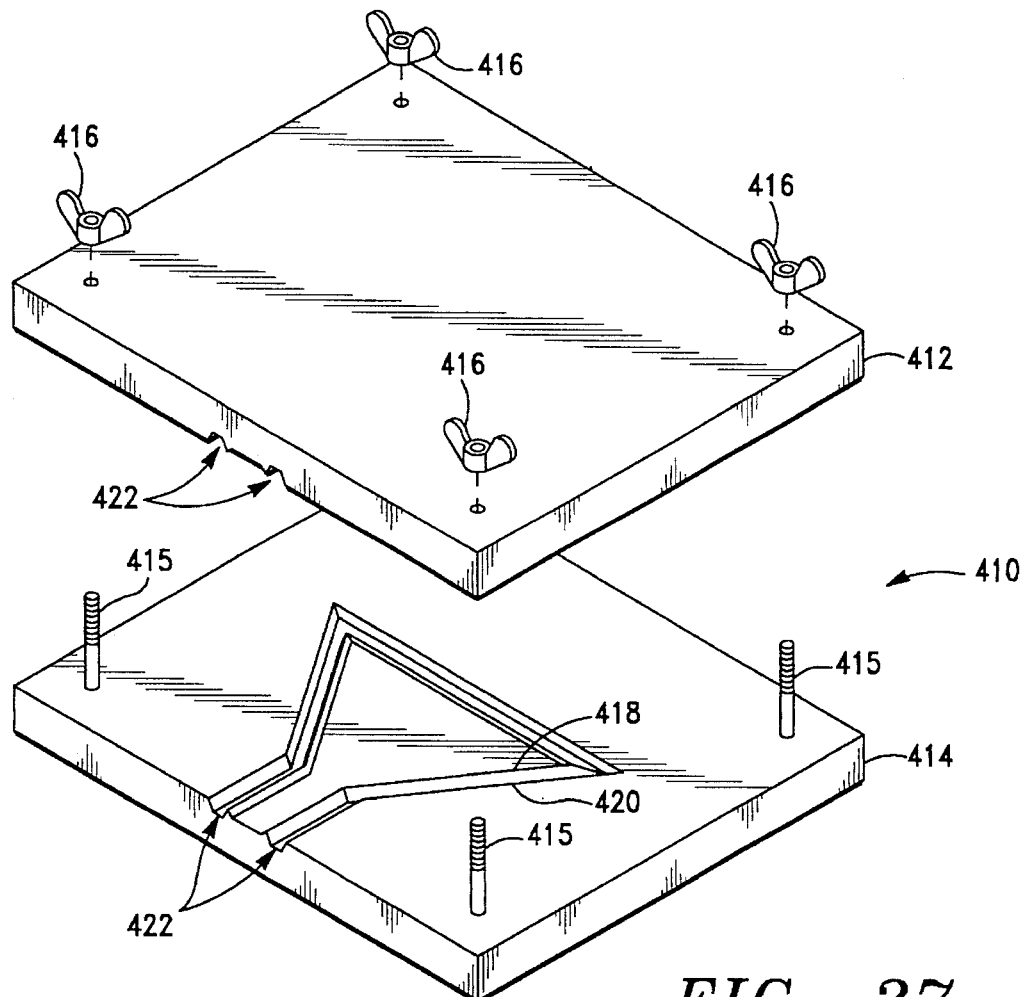
FIG. 27 is an isometric view of a jig for use in sealing the edges of the ablation balloon.

A third technique and one found to work particularly well involves the use of an adhesive to secure the electrodes to the base while the substrate material is spread over the electrodes and base, and while the substrate material is curing. Referring to FIG. 26, the adhesive material may take the form of adhesive islands 390 formed on a sheet 392. By placing the sheet 392 onto the base 394, the adhesive islands (which correspond to the electrode holding zones 396 on the base 394) are transferred to the zones 396. Guide posts 398 on the base align the sheet 392 with the base 394 by passing the holes 400 over the posts 398. The electrodes, which may take the form of copper plates, may then be individually placed in the zones 396 or be transferred by means of a second sheet 402 having guiding holes 404. A plurality of electrodes 406 are secured to the sheet 402 by means of a week adhesive. If this technique is adopted, the steps involved include placing the sheet 392 over the posts 398 to transfer the adhesive islands 390 to the zones 396. The sheet 392 is then removed, and the sheet 402 placed over the post 398 to transfer the electrodes 406 to the zones 396. The uncured emulsion forming the substrate material is then spread onto the base 394 by pouring the material onto the base 394. The material flows to form a thin sheet. In each of the various bladder forming techniques the substrate is typically formed to have a thickness of approximately ten mils. Either a heat cured or a room temperature cured silicone rubber can be used. The heat cured silicone rubber has the advantage that it is stronger and dries in approximately one hour. The room temperature cured silicone rubber on the other hand allows the electrodes to be secured using conventional adhesives which are not affected by the heat curing process. In order to circumvent the problems associated with the inherent stickiness of the final silicone rubber product, a powder, silicone oil or other lubricant can be applied to the surfaces of the bladder.

Figure 28:
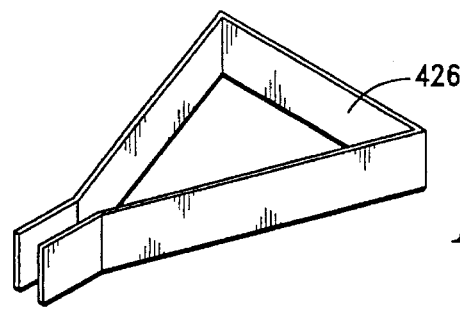
FIG. 28 is an isometric view of a cutting device for use in the manufacturing process of the ablation balloon.

Once the substrate material has been removed from the base with the electrodes embedded in it or secured thereto, it is folded along the line 342 as described with reference to FIG. 21. The edges 344 and 346 are then connected. This is achieved in a manner described with reference to FIG. 27. A jig 410 comprising an upper section 412 and a lower section 414 is provided. The substrate material is peeled off the base and folded to form a triangle with one corner missing. It is then placed between the two jig halves which are thereafter secured to one another by means of bolts 415 and wingnuts 416. The sections 412 and 414 of the jig 410 have complimentary cut-outs 418 (only one shown) to accommodate the folded substrate material so as to pinch the substrate material along the triangular sides of the jig 410. Grooves 420 formed in the halves 412, 414 define peripheral channels along the three sides of the triangular cutout portions when the two halves 412, 414 are secured to one another. Adhesive is forced into the peripheral channels via a communication channel defined by communication grooves 422. Once the adhesive has set, the halves 412, 414 are removed and the edges of the substrate trimmed to form a substantially triangular bladder. Typically a trimming jig 426 is used as illustrated in FIG. 28. The trimming jig 426 essentially comprises a blade shaped to correspond to the periphery of the bladder.

Figure 29:
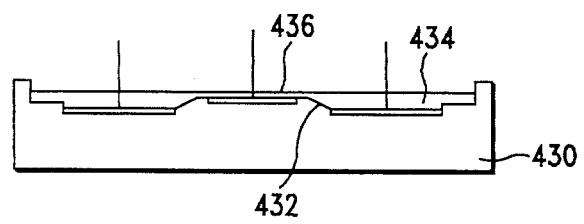
FIG. 29 is a sectional side view of another embodiment of a support base.

It is desirable to be able to produce a bladder having zones of greater and lesser stretchability. This can be achieved in a number of ways. One method involves molding the substrate of the bladder in a manner to form a bladder having different wall thicknesses. FIG. 29 illustrates a sectional side view of a base 430 having a raised portion 432, thereby producing a substrate 434 having a portion 436 of reduced thickness. By appropriately shaping the surface of the base 430, the thickness of the substrate 434 can be suitably adjusted.

A similar effect can be achieved by molding ribs or grooves into the substrate material. Grooves can also be subsequently cut into the surface of the substrate material.

Figure 30:
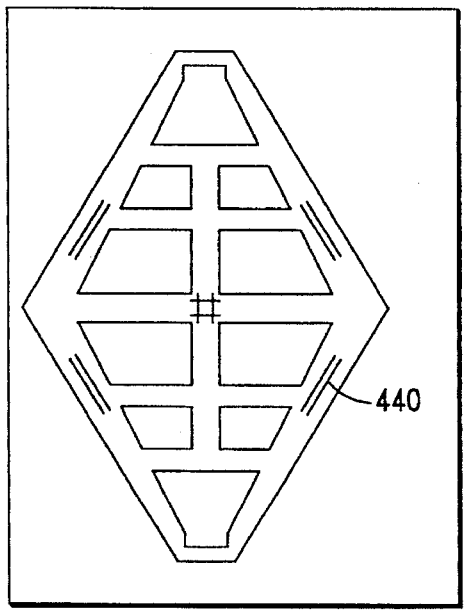
FIG. 30 is a plan view a stretchable substrate layer for use in the manufacture of an ablation balloon.
Figure 31:
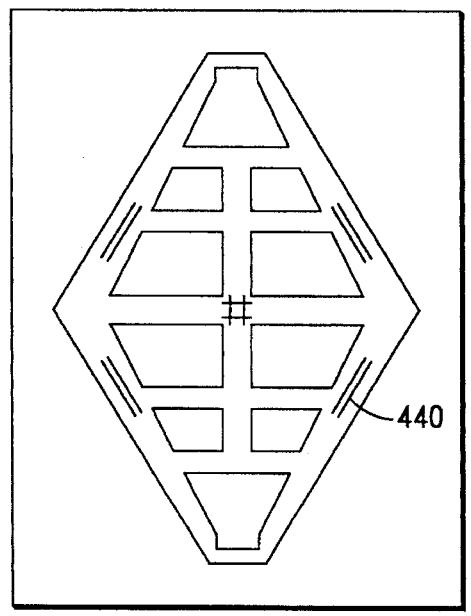
FIG. 31 is a plan view of another embodiment of a stretchable substrate layer for use in the manufacture of an ablation balloon.

The resultant substrate material would then appear, for instance, as that illustrated in FIGS. 30 and 31. The grooves 440 (FIG. 30) or ribs 442 (FIG. 31) can be directed along lines to produce a certain stretchability. The stretchability would clearly be greater in a direction transverse to the ribs or grooves 440, 442 and less in a direction along the ribs or grooves 440, 442.

Figure 32:
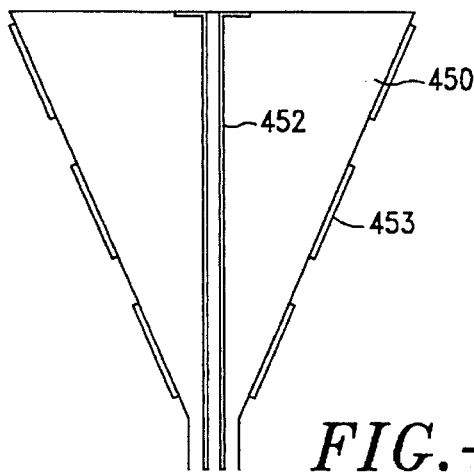
FIG. 32 is a sectional side view of an ablation balloon having a central pipe.
Figure 33:
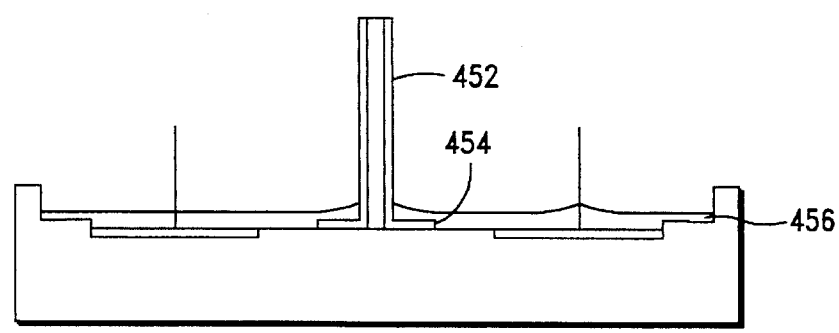
FIG. 33 is a sectional side view of the ablation balloon of FIG. 32 during the manufacturing process.

A further variation to the bladder is illustrated in FIG. 32. This shows a bladder 450 having a centrally extending tube 452 for passing an optical fiber to the tip of the bladder 450 or for passing an electrically conductive lubricant through the bladder 450 to provide better electrical contact between the electrodes 453 on the outer surface of the bladder and the wall of the uterus (not shown). Instead of monitoring the position of the bladder in the uterus using an optical fiber, the bladder can be passed into the uterus blindly. Thereafter, to ensure that the uterus has not been punctured, a fluid, for example saline solution, may be passed along the tube 452 and into the uterus. By monitoring the fluid pressure in the uterus, it can be determined whether or not the uterus wall has been punctured. The tube 452 is formed in the bladder 450 by mounting the tube 452 on the base during the forming process as illustrated in FIG. 33. The tube 452 has a flared end 454. This provides a greater sealing surface with the substrate material 456.

Clearly the electrodes formed on the bladder can be formed in various shapes. FIG. 34 schematically illustrates the typical electric field pattern generated by a rectangular electrode 460. The electric field lines vary in strength, the length of the lines in FIG. 34 indicating the strength of the field. It is clear that the field is strongest at the corners of the electrode 460 and weakest on the surface of the electrode 460. The resultant heating effect is shown schematically in cross section in FIG. 35 in which the electrode 460 is shown in contact with the uterine wall 462. The heating is shown to be stronger along the edges of the electrode 460. In order to achieve a more uniform electric field distribution an electrode 463 having perforations 464 as illustrated in FIG. 36 may be formed. Greater electric field uniformity is thereby achieved resulting in a more even heating pattern. This configuration also has the advantage that the electrode is more stretchable.

Figure 37:
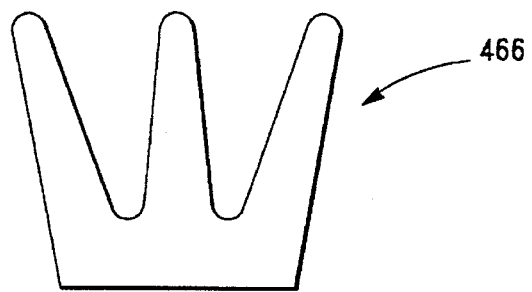
FIG. 37 is a plan view of another embodiment of an electrode.

Another electrode pattern is illustrated in FIG. 37 which provides for greater stretchability of the electrode 466 in a direction transverse to its longitudinal axis. The electrodes discussed above are typically made of a conductive, flexible, corrosion resistant material such as copper, silver or other metal. These may be coated with gold or palladium to provide electrodes having a total thickness of three microns. Irrespective of the electrode configuration adopted tests have shown that due to conductive heating between adjacent electrodes, an 8 to 9 millimeter gap is sufficiently small to provide adequate ablation. Although each electrode is individually powered sequentially, the high rate of switching (approximately 50 times per second) ensures that there is no significant cooling of the tissue between successive applications of power to the same electrode.

Figure 38:
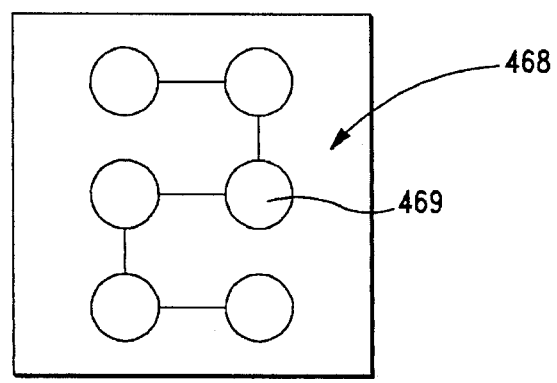
FIG. 38 is a plan view of yet another embodiment of an electrode.

Yet another electrode is illustrated in FIG. 38 in which each electrode 468 is made up of a plurality of interconnected electrode dots 469. The dots 469 are made of a conductive material while the intermediate material is a stretchable non-conductive material, thereby providing an electrode having greater flexibility.

Figure 39:
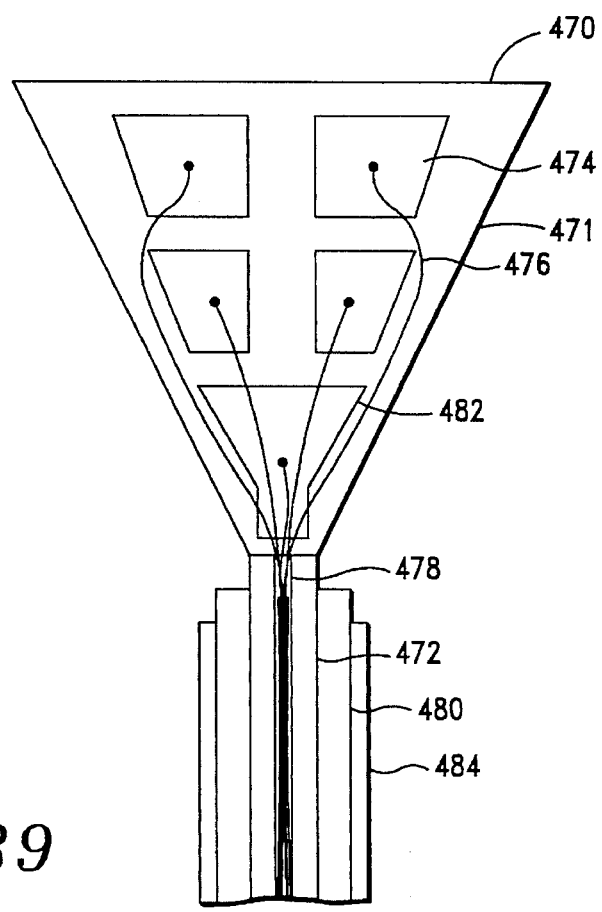
FIG. 39 is a sectional side view of an ablation device in accordance with the invention.

As illustrated in FIG. 39, the completed device comprises a bladder 470 secured to a fluid supply tube 472 for inflating the bladder 470. The electrodes 474 are mounted on the bladder 470 to provide exposed electrode surfaces on the outer surface of the bladder 470. The electrode leads 476 extend internally within the bladder 470 and down a conductor sleeve 478 in the fluid supply tube 472. The leads for the temperature sensors (not shown) pass down the sleeve 478. In a preferred embodiment, an outer sleeve 480 passes over the tube 472 and is slidably mounted relative to the tube 472. This allows the sleeve 480 to be pushed forward so as to cover at least part of the base electrode 482. In this way, ablation at the base of the uterus can be adjusted. The catheter used for inserting the device into the uterus is indicated by reference numeral 484.

Utilizing the present invention allows for the use of low accuracy thermistors wherein calibrations can be stored in memory chips in the handle of the device. The attachment of the electrodes to the bladder can be accomplished by conductive adhesive or by soldering.

The bladder 142 of FIGS. 10 and 11 can be deployed by retracting the catheter sheath 133 relative to the bladder 142. Once the treatment has been completed, the sheath 133 is pushed back over the bladder 142, collapsing the bladder. In order to expedite the deployment, the bladder can be formed with particular kinds of spines formed to engage complementary formations on the sheath in order to aid in the folding of the patterned bladder within the catheter sheath 133.

Obviously, numerous modifications and variations of the present invention are possible in light of the above teachings. One of the more obvious variations based upon the above disclosure is the utilization of such an electrode partitioning structure and the accompanying heating for treatment of other body organs or tissues either externally or internally. The principles embodied herein and the methods utilizing those principles with respect to the delivery of controlled RF energy in a controlled environment have application in many areas, not only for controlled destruction of tissue but also for controlled heat treatment of tissue. It is therefore to be understood that, within the scope of the appended claims, the invention may be practiced otherwise than as specifically described herein.

What is claimed as new and desired to be secured by Letters Patent of the United States is:

1. An apparatus for selectively applying RF energy to a body organ, said apparatus comprising:

an electrode means for effecting electrical contact with tissue of said body organ;

a radio frequency power means for providing current to said electrode means at a frequency greater than 250 kHz; and switching means for receiving an output from said radio frequency power means and for controlling the current to said electrode means, wherein said switching means includes a first means for providing bipolar energy to said electrode means, a second means for providing monopolar energy to said electrode means, and a third means for selecting one of said first and second means, and wherein selected portions of said tissue are heated at a uniform temperature between 45° C. and 90° C. by passing current through the selected portions of the tissue.

2. The apparatus according to claim 1 wherein the electrode means comprises a plurality of electrodes and wherein said first means further includes a means for delivering said RF energy in a bipolar mode between selected ones of said plurality of electrodes.

3. A method of heating body organ tissue by the selective application of RF energy to said tissue, comprising the steps of:

provinding a plurality of electrodes in electrical contact with said body organ;

providing a source of radio frequency energy to said plurality of electrodes, said source including switching means for switching between monopolar and bipolar delivery of energy to the electrodes;

selecting one of monopolar and bipolar delivery of energy by means of the switching means; and controlling said radio frequency energy to the electrodes so as to heat selected portions of the body organ to a uniform temperature between 45° C. and 90° C. by passing current through the selected portions of the body organ.

4. The method according to claim 3 wherein the step of controlling said radio frequency energy includes selectively providing bipolar energy to selected pairs of said plurality of electrodes.

* * * * *